United States Patent
Pan et al.

(10) Patent No.: US 10,434,323 B2
(45) Date of Patent: Oct. 8, 2019

(54) DEVICES AND METHODS FOR MAGNETIC STIMULATION FOR THE TREATMENT OF NEUROLOGICAL DISORDERS

(71) Applicant: Neuroprex Inc., Santa Clara, CA (US)

(72) Inventors: Hong-Tsz Pan, Cupertino, CA (US); Zhaoyin Wu, San Jose, CA (US); Hsiu-Wen Huang, Cupertino, CA (US)

(73) Assignee: NeuroPrex Inc., Santa Clara, CA (US)

( * ) Notice: Subject to any disclaimer, the term of this patent is extended or adjusted under 35 U.S.C. 154(b) by 87 days.

(21) Appl. No.: 15/716,079

(22) Filed: Sep. 26, 2017

(65) Prior Publication Data

US 2018/0071546 A1    Mar. 15, 2018

Related U.S. Application Data

(63) Continuation of application No. 14/882,286, filed on Oct. 13, 2015, now Pat. No. 9,814,898, which is a
(Continued)

(51) Int. Cl.
*A61N 2/02*    (2006.01)
*A61N 2/00*    (2006.01)

(52) U.S. Cl.
CPC ............... *A61N 2/02* (2013.01); *A61N 2/004* (2013.01); *A61N 2/006* (2013.01); *A61N 2/008* (2013.01)

(58) Field of Classification Search
CPC ........ A61N 2/004; A61N 2/006; A61N 2/008; A61N 2/02
See application file for complete search history.

(56) References Cited

U.S. PATENT DOCUMENTS

| | | |
|---|---|---|
| 4,412,540 A | 11/1983 | Bentall |
| 4,994,015 A | 2/1991 | Cadwell |

(Continued)

FOREIGN PATENT DOCUMENTS

| | | |
|---|---|---|
| EP | 0709115 A1 | 5/1996 |
| WO | 0192817 A1 | 12/2001 |

OTHER PUBLICATIONS

TIPO—Search Re[Prt, for corresponding Int. Applciation No. PCT/US2013/052363.
(Continued)

*Primary Examiner* — Christine H Matthews
(74) *Attorney, Agent, or Firm* — Patterson + Sheridan, LLP

(57) ABSTRACT

Described herein are magnetic neural stimulation systems for the treatment of neurological disorders. One variation of a magnetic neural stimulation system includes magnetic stimulators shaped as helical or ramped coils, where each turn of the coil has an acute turning angle of less than 90 degrees. Also described herein are magnetic neural stimulation systems that include an array of stimulators and one or more shielding components. The shielding components modulate the density profile of the induced eddy currents to increase stimulation to targeted neural tissue regions while decreasing stimulation to non-targeted neural regions. Other variations of magnetic stimulation systems include one or more stimulators and a shield in which some of the induced eddy currents in the shield may act to attenuate the magnetic field in certain regions of the shield.

18 Claims, 34 Drawing Sheets

Related U.S. Application Data continuation of application No. 14/468,294, filed on Aug. 25, 2014, now Pat. No. 9,205,275, which is a continuation of application No. PCT/US2013/052363, filed on Jul. 26, 2013.

(60) Provisional application No. 61/741,872, filed on Jul. 30, 2012, provisional application No. 61/785,651, filed on Mar. 14, 2013.

(56) References Cited

U.S. PATENT DOCUMENTS

| | | | |
|---|---|---|---|
| 5,000,178 | A | 3/1991 | Griffith |
| 5,857,957 | A | 1/1999 | Lin |
| 6,048,302 | A | 4/2000 | Markoll |
| 6,066,084 | A | 5/2000 | Edrich et al. |
| 6,179,770 | B1 | 1/2001 | Mould |
| 6,179,771 | B1 | 1/2001 | Mueller |
| 6,235,251 | B1 | 5/2001 | Davidson |
| 7,976,451 | B2 | 7/2011 | Zangen et al. |
| 8,052,591 | B2 | 11/2011 | Mishelevich et al. |
| 9,205,275 | B2 * | 12/2015 | Pan .................. A61N 2/006 |
| 2001/0018547 | A1 | 8/2001 | Mechlenburg et al. |
| 2001/0031906 | A1 | 10/2001 | Ishikawa et al. |
| 2002/0103411 | A1 | 8/2002 | Bailey et al. |
| 2003/0217754 | A1 | 11/2003 | Thomas et al. |
| 2006/0094924 | A1 | 5/2006 | Riehl |
| 2008/0103350 | A1 | 5/2008 | Farone |
| 2009/0108969 | A1 | 4/2009 | Sims et al. |
| 2009/0112278 | A1 | 4/2009 | Wingeier et al. |
| 2010/0160712 | A1 | 6/2010 | Burnett et al. |
| 2011/0021863 | A1 | 1/2011 | Burnett et al. |
| 2011/0046432 | A1 | 2/2011 | Simon et al. |
| 2011/0065976 | A1 | 3/2011 | Chornenky et al. |
| 2011/0082326 | A1 | 4/2011 | Mishelevich et al. |
| 2012/0245403 | A1 | 9/2012 | Martinez |

OTHER PUBLICATIONS

Patent Cooperation Treaty—International Search Report, Int. Application No. PCT/US2013/052363 dated Jul. 26, 2013.
"Magnetic stimulation of the motor cortex—theoretical considerations", published by IEEE Transactions on Biomedical Engineering, 1991.
Suppressing the Surface Field During Transcranal Magnetic Stimulation of IEEE Transaction on Biomedical Engineering, 2006.
Background physics for magnetic stimulation, Jarmo Rubhonen, 2003.
TMS and threshold hunting, Friedemann Awiszus, 2003.
Non-invasive magnetic stimulation of human motor cortex. Barker et al. Lancet 1985; 1: 1106-1107.
Safety, ethical considerations, and application guidelines for the use of transcanial magnetic stimulation in clinical practice and research, 2.3 types of coils, Rossi, et al., 2009.
A coil design for transcranial magnetic stimulation of deep brain regions, Roth et al., 2002.
A model for focal magnetic brain stimulation, Murro, et al., 1992.
Modeling the effects of electrical conductivity of the head on the induced electric field in the brain during magnetic stimulation, Davey, et al., 2003.
Prediction of Magnetically Induced electric fields in biological tissue, Davey, et al., 1991.
Improved field localization in transcranial magnetic stimulation of the brain with the utilization of a conductive shield plate in the stimulator. Kim, et al. IEEE transaction on biomedical engineering vol. 33., No. 4, 2006.
A numerically optimized active shield for improved transcranial magnetic stimulation targeting. Hernandez-Garcia, et al. 2010.
Experimental study to improve the focalization of a figure-eight coil of rTMS by using a highly conductive and highly permeable medium. Zhang, et al. 2013.

* cited by examiner

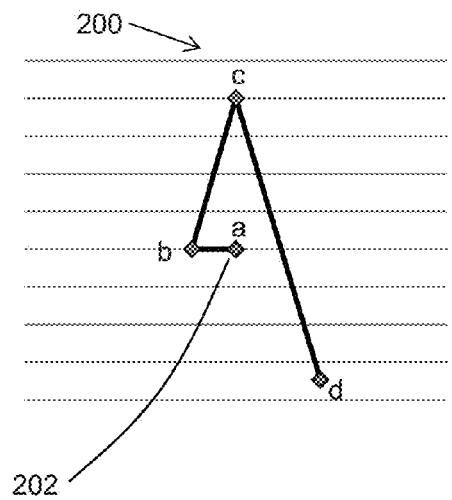
FIG. 2A
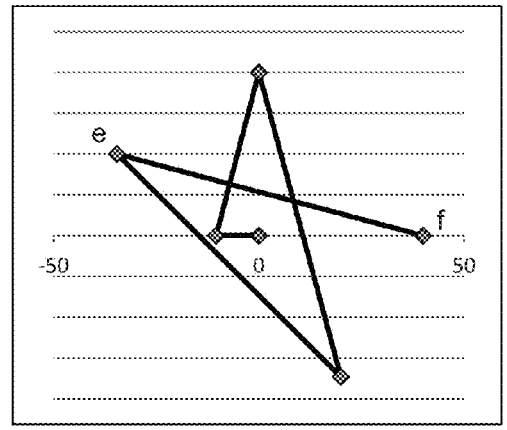
FIG. 2B
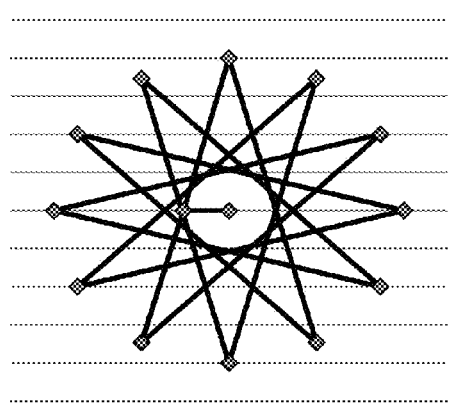
FIG. 2C
| Point | X | Y | Z |
|---|---|---|---|
| a | 0 | 0 | 0 |
| b | -10.4 | 0 | 0 |
| c | 0.00 | 40.00 | 0 |
| d | 20.00 | -34.64 | 1 |
| e | -34.64 | 20.00 | 2 |
| f | 40.00 | 0.00 | 3 |
| g | -34.64 | -20.00 | 4 |
| h | 20.00 | 34.64 | 5 |
| i | 0.00 | -40.00 | 6 |
| j | -20.00 | 34.64 | 7 |
| k | 34.64 | -20.00 | 8 |
| l | -40.00 | 0.00 | 9 |
| m | 34.64 | 20.00 | 10 |
| n | -20.00 | -34.64 | 11 |
| o | -10.40 | 0.00 | 12 |
FIG. 2D

| Material | Relative Permitivity | Relative Permeability | Conductivity (s/m) | Dielectric Loss Tangent | Magnetic Loss Tangent |
|---|---|---|---|---|---|
| BoneCortical | 144.51 | 1 | 0.024353 | 3.0293 | 0 |

| Material | Relative Permitivity | Relative Permeability | Conductivity (s/m) | Dielectric Loss Tangent | Magnetic Loss Tangent |
|---|---|---|---|---|---|
| BrainWhiteMatter | 479.79 | 1 | 0.10214 | 3.8266 | 0 |

Bi-polar, gradient sin wave pulse (one pulse every 150 ms)

| Material | Relative Permitivity | Relative Permeability | Conductivity (s/m) | Dielectric Loss Tangent | Magnetic Loss Tangent |
|---|---|---|---|---|---|
| Sea Water | 81 | 0.999991 | 4 | 0 | 0 |

FIG. 9

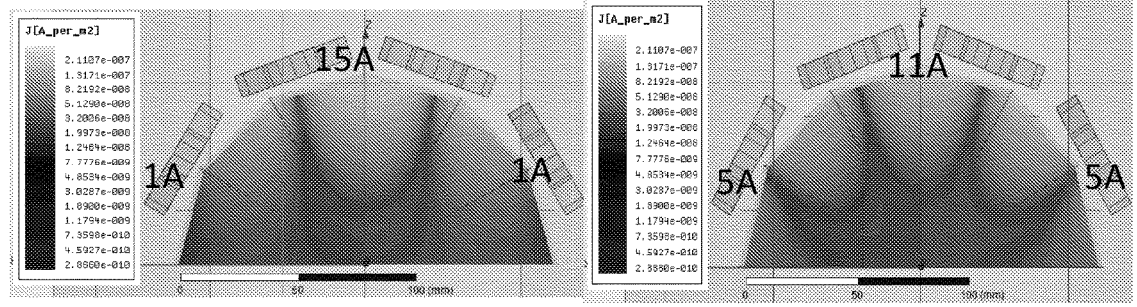
FIG. 10A
FIG. 10C
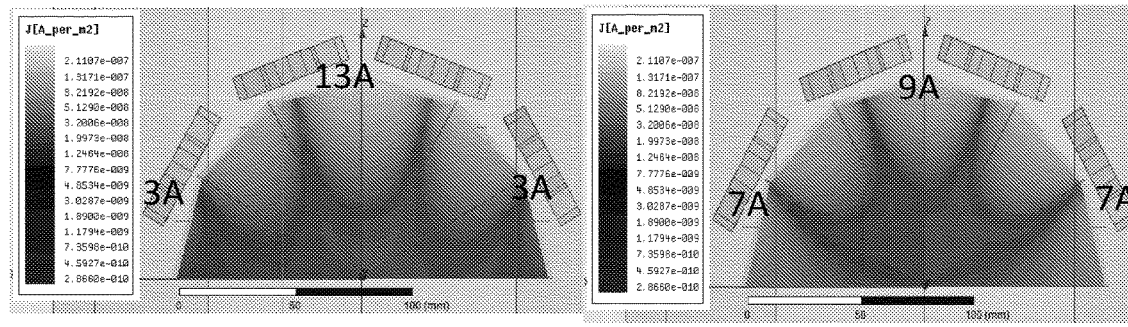
FIG. 10B
FIG. 10D

|  | No shielding | | | | Shielding | | | |
| --- | --- | --- | --- | --- | --- | --- | --- | --- |
|  | 2.5cm deep | top surface | 30degree surface | 60degree surface | 2.5cm deep | top surface | 30degree surface | 60degree surface |
| Pattern-1 | 1.00 | 2.97 | 1.43 | 0.08 | 1.00 | 2.58 (87%) | 1.17 | 0.12 |
| Pattern-2 |  |  |  |  |  |  |  |  |
| Pattern-3 | 1.00 | 3.26 | 2.21 | 0.76 | 1.00 | 3.26 | 2.15 | 0.62 |
| Pattern-4 |  |  |  |  |  |  |  |  |
| Pattern-5 | 1.00 | 4.10 | 4.76 | 3.57 | 1.00 | 4.29 | 5.00 | 3.36 |
| Pattern-6 |  |  |  |  |  |  |  |  |
| Pattern-7 |  |  |  |  |  |  |  |  |
| Pattern-8 | 1.00 | 0.56 | 6.03 | 8.91 | 1.00 | 0.79 | 5.00 | 6.42 (72%) |

FIG. 12

DEVICES AND METHODS FOR MAGNETIC STIMULATION FOR THE TREATMENT OF NEUROLOGICAL DISORDERS

CROSS-REFERENCE TO RELATED APPLICATIONS

This application is a continuation of U.S. patent application Ser. No. 14/882,286, filed Oct. 13, 2015, which is a continuation application of U.S. patent application Ser. No. 14/468,294, filed Aug. 25, 2014, which is a continuation application of PCT patent application no. PCT/US2013/052363, filed Jul. 26, 2013, which claims priority to U.S. Provisional Patent Application No. 61/741,872 filed Jul. 30, 2012 and U.S. Provisional Patent Application No. 61/785,651 filed Mar. 14, 2013, which are each hereby incorporated by reference in its entirety.

BACKGROUND

Presently, magnetic stimulation devices are employed in the treatment of brain neuron disorder such as depression, obsessive-compulsive disorder, insomnia, bipolar disease, epileptic or febrile seizures etc. For example, transcranial magnetic stimulation (TMS) is a non-invasive method that uses brief, intense pulses of electric current delivered in a coil placed on a patient's head to induce a time-varying magnetic field that gives rise to eddy currents within the patient's brain. Magnetic stimulators with various shapes and geometries have been used in an attempt to generate different eddy current density profiles in order to target neural tissues located at different depths in the skull. While certain magnetic stimulators have been able to stimulate neurons in deeper cranial structures, in many cases the magnitude of the applied current to reach those structures generates excessive surface heat is uncomfortable for the patient. In addition, deeper brain stimulation may also be more diffuse in its treatment field, thereby activating non-targeted neurons in conjunction with the targeted neurons. Other magnetic stimulators may provide more focused eddy current densities, but only at or near the surface of the skull.

Efforts are currently underway to develop magnetic neural stimulation systems that can provide focused stimulation of neural tissues that are beneath the skull. Magnetic stimulators that can provide a practitioner with the ability to selectively stimulate certain neural populations without overheating or stimulating peripheral tissue regions may be desirable.

BRIEF SUMMARY

The magnetic neural stimulation systems described herein may be used for the treatment of neurological disorders (including, but not limited to, headaches, migraines, depression, obsessive-compulsive disorder, insomnia, bipolar disease, post-traumatic stress syndrome, Parkinson's disease, schizophrenia, dystonia, autism, pain, and epileptic or febrile seizures). In one embodiment, a magnetic stimulation system includes a first coil comprising a single wire having a plurality of turn, and a shield including an external surface and an internal surface both comprising a non-conductive material, an internal cavity defined between the external surface and the internal surface, a first opening, penetrating through the shield and communicating the external surface and the internal surface, and a first channel, formed on the external surface and intersecting the first opening, wherein the depth of first channel extends through the entire thickness of the shield to divide the internal cavity, and a conductive substance, filled in the internal cavity.

BRIEF DESCRIPTION OF THE DRAWINGS

FIG. 1F depicts another variation of a ramped or helically coiled magnetic stimulator with a plurality of acute turns that are rounded.

FIGS. 2A-2C depict one example of a method for making a ramped or helically coiled stimulator from a single wire.

FIG. 2D depicts a table listing the coordinates of each turn of the stimulator of FIGS. 2A-2C.

FIG. 9 depicts simulation parameters used to model the eddy current density profile generated by an array of Figure-eight stimulators without shielding components as compared to a Figure-eight an array of Figure-eight stimulators with shielding components.

FIG. 12 depicts a table that summarizes the eddy current density at different regions of tissue for each of the various simulation configurations depicted in FIGS. 10a-h and 11a-h.

FIG. 13A is a perspective view of the magnetic stimulation system, FIG. 13B is a side view of the system of FIG. 13A and FIG. 13C depict the system of FIG. 13A disposed over a head model.

DETAILED DESCRIPTION

Figure 1A:
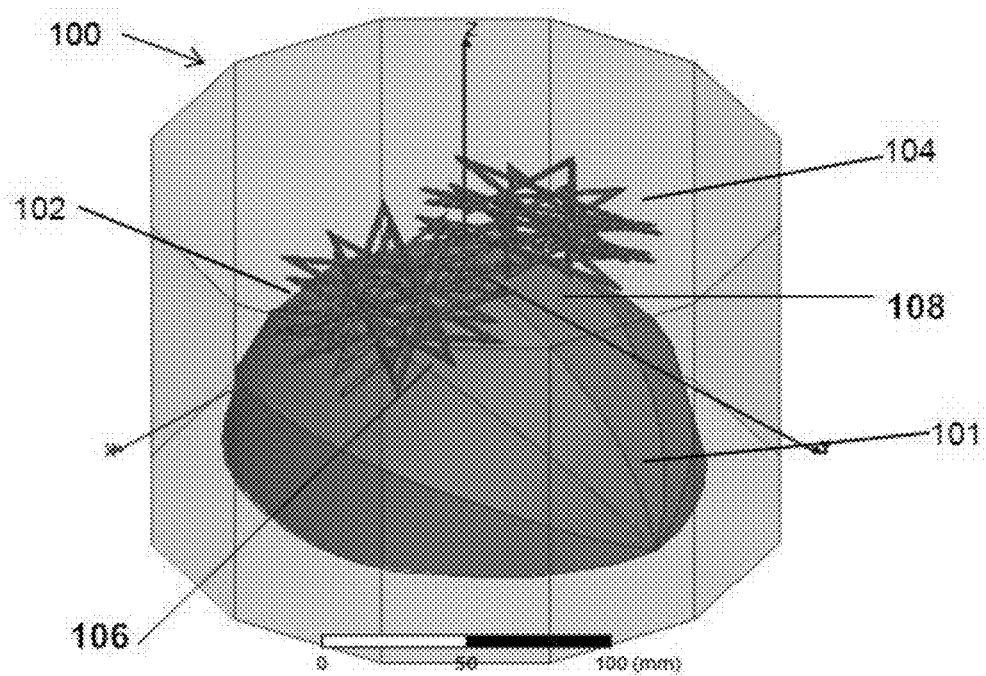
FIGS. 1A-1F depicts one variation of a ramped or helically coiled magnetic stimulator.

Described herein are various devices and systems for magnetic neural stimulation.

One variation of a system using a plurality of magnetic stimulators is depicted in FIGS. 1A-1E. A system for magnetic neural stimulation may have one or more magnetic stimulators, e.g., two stimulators. For example, the magnetic neural stimulation system 100 may have a first magnetic stimulator 102 and a second magnetic stimulator 104 that is connected to the first magnetic stimulator. Each of the magnetic stimulators may be a ramped or helical coil made of a single wire having a plurality of acute turns, where the turning angle is less than 90 degrees. Using a single wire (e.g., a copper wire that may or may not have a core of a different material) may ensure that the current across the wire is the same across the entire helical coil, such that the induced magnetic field is the same across the length of the wire. This may help reduce any variability of induced magnetic field such that a practitioner may control the stimulation of target neurons more consistently than stimulators that comprise more than one wire. Alternatively, a helically coiled stimulator may comprise multiple segments of wire, e.g., two, three, four, five, six or more separate wires. The first and second magnetic stimulators may each have a first end and a second end, where the first end is a positive terminal and the second end is a negative terminal. For example, the first end of the first stimulator 102 may be connected to the positive terminal of a high voltage generator and the second end of the first stimulator may be connected to the first end of the second stimulator 104. The second end of the second stimulator 104 may be connected to the negative terminal of a high voltage generator. The wire forming the first stimulator may continuously extend to form the second stimulator. Any desired number of stimulators may be formed from the same wire such that the magnetic field induced by a current in the wire is the same across all of the stimulators.

The helically coiled magnetic stimulators 102, 104 may have any number of turns 110, for example, 5, 6, 7, 8, 9, 10, 11, 12, 13, 14, 15, 20, 21, etc. In some variations, the turning angle TA may be less than 90 degrees, for example, 10 degrees, 15 degrees, 20 degrees, 25 degrees, 30 degrees, 35 degrees, 40 degrees, 45 degrees, 50 degrees, 55 degrees, 60 degrees, 89 degrees etc. In some variations, the turns 110 may be sharp (e.g., forming a corner with sharp edges) or curved (e.g., forming a corner with rounded edges). In some variations, the turns 110 may have a radius of curvature from about 1 mm to about 8 mm, similar to the helically coiled stimulator depicted in FIG. 1F. The pitch (e.g., the rise or distance between each turn) may vary depending on the diameter of the wire. In some variations, there may be additional space between the turns for circulating air for cooling the stimulator. For example, magnetic stimulators 102, 104 may have 12 turns, where each turn has a turning angle of 30 degrees and the pitch may be about 1 mm, resulting in a total height H of 12 mm. The distance from each turn 110 to the central axis 112 of the helical coil may be the constant. In some variations, the distance from each turn of a coil may vary, and may increase or decrease for each successive turn. For example, a magnetic stimulator may be a spiraled coil, where the distance from each turn to the central axis increases with each turn (e.g., a gradually widening spiral coil), decreases with each turn (e.g., a gradually tapering spiral coil), or may be the same across all turns (e.g., a helical coil). A helical coil may refer to any geometry that has a series of ramped shapes or structures, which may or may not have smooth curves. A helical coil may comprise a series of ramped structures where each structure is repeated (e.g., uniform repeating shapes), or may comprise a series of ramped structures where each structure is different (e.g., non-uniform shapes that are repeatedly ramped). A helical coil may refer to any geometry that has a shape or structure that is continuously repeated and stacked, and/or ramped and rotated (e.g., twisted). In some variations, each repeat of the shape or structure may be offset from its adjacent repeat. For example, a helical coil may comprise an angular shape having sharp angles (e.g., a triangle, rectangle, star polygon) that is repeated and rotated as it ramps. Each iteration of the angular shape along the ramped or helical coil is stacked over the previous iteration, but is rotated such that the angles of one iteration are not aligned with the angles of the previous iteration (e.g., the corresponding angles of the two iterations are rotationally offset). The repeated shapes or structures of a helical coil may share a common axis (which may or may not be perpendicular to the surface of the treatment site). For example, the center of each iteration of the angular shape of a helical coil may be aligned with the center of the other iterations, but may be rotationally offset from its adjacent iterations. Alternatively or additionally, a helical coil may refer to a series of repeated and ramped hypotrochoid (e.g., hypocycloid, deltoid, asteroid, etc.) or epitrochoid (e.g., epicycloid, cardioid, etc.) shapes. Although the helically coiled magnetic stimulators described and depicted herein have a particular geometry, it should be understood that a helically coiled magnetic stimulator may have any of the geometries described above.

Figure 1B:
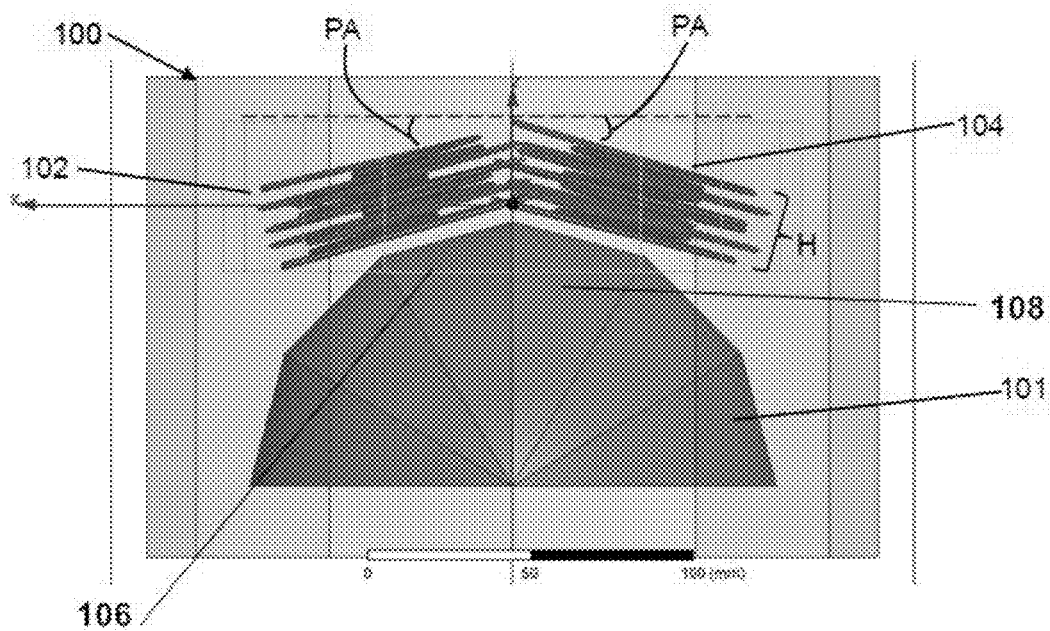
Figure 1C:
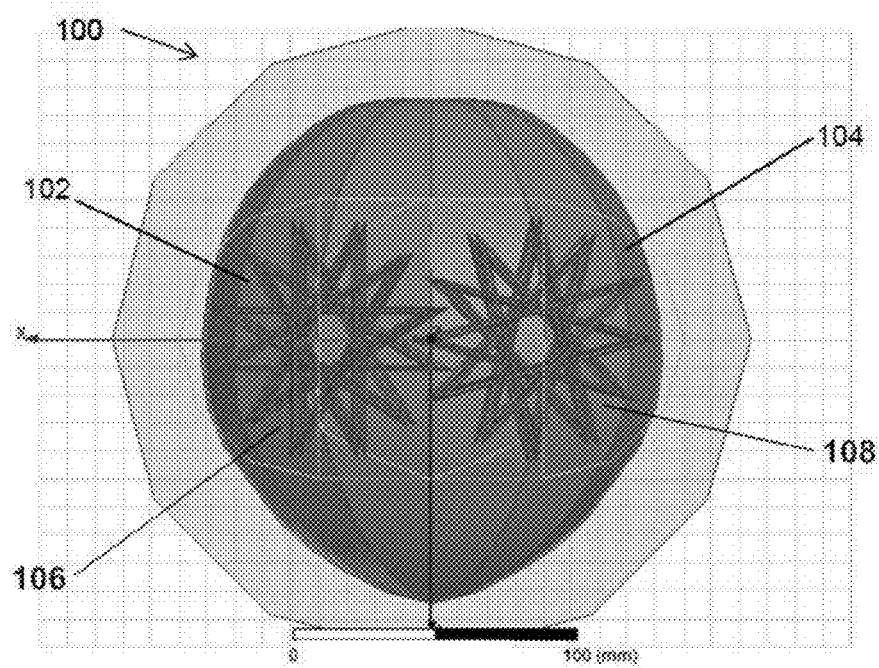
Figure 1D:
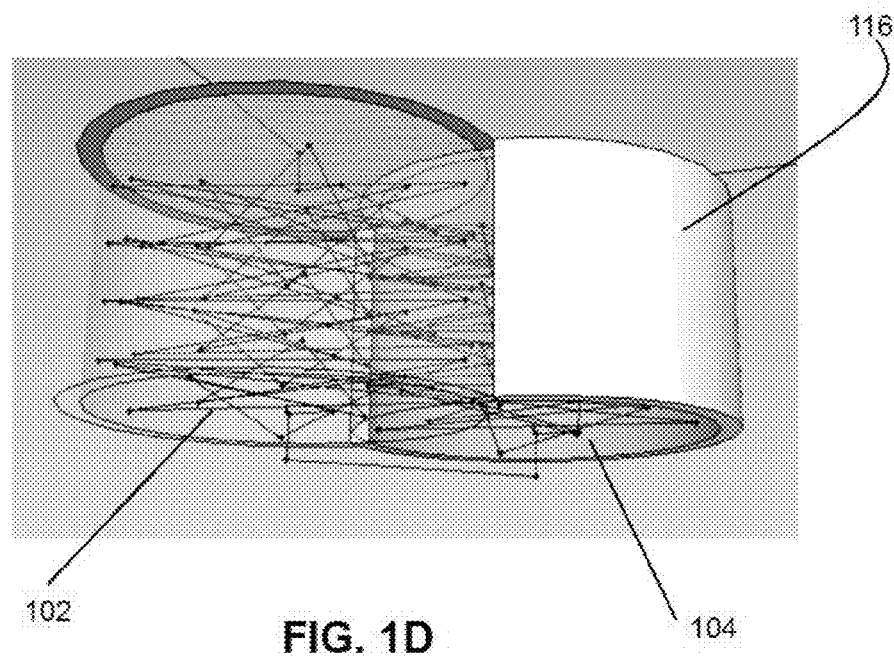
Figure 1E:
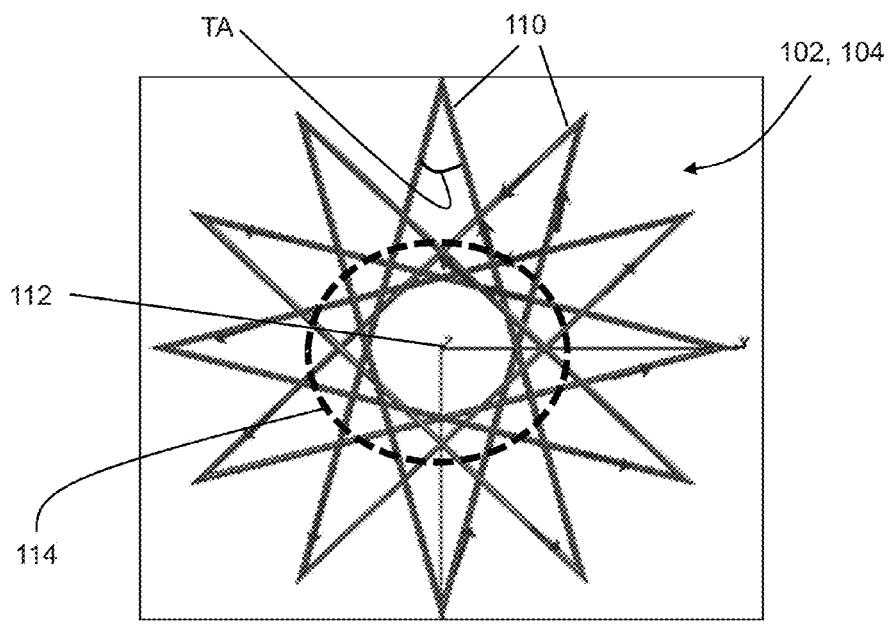
Figure 1F:
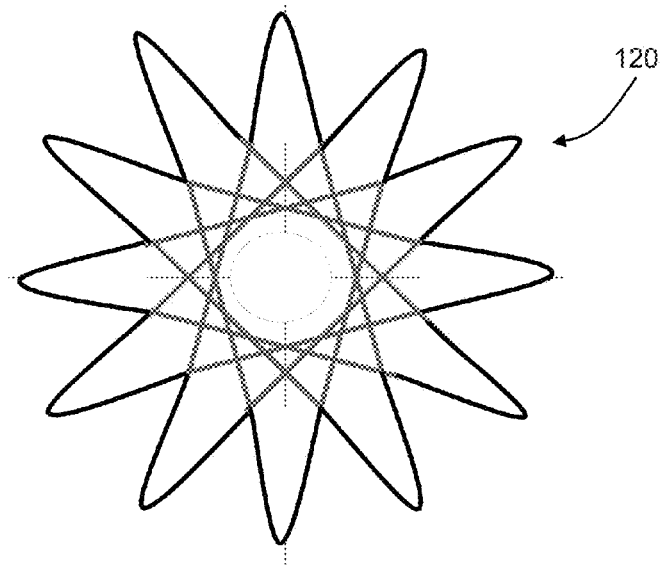

FIG. 1E depicts a top view down the central axis of one of the helically coiled magnetic stimulators 102, 104. As illustrated there, the profile of the magnetic stimulator (as viewed down the central axis 112) may have a star polygon shape, where each turn of the helical coil is a vertex of the star polygon. For example, a coiled stimulator may have 12 turns and may have a star polygon profile with 12 vertices. The central region 114 of the star polygon profile may have a high concentration of wire crossings. The currents traversing the mesh of wire crossings in the central region 114 may induce magnetic field lines pointing in opposite directions (e.g., both downward into the page and upward out of the page). These opposing field lines may repel each other, resulting in a cumulative magnetic field that is weaker on the inside of the helically coiled stimulator than on the outside of the coil. This unexpected synergy between the induced magnetic field lines of the meshed wire crossing may act to enhance and/or strengthen the magnetic field just outside the helically coiled stimulator, which may allow the magnetic field to penetrate more deeply into a patient's head. FIG. 1F depicts a top view down the central axis of another variation of a helically coiled magnetic stimulator 120, where each turn has an acute turning angle of less than 90 degrees, but is curved with a radius of curvature from about 1 mm to about 5 mm.

The magnetic neural stimulation system 100 may be positioned with respect to a patient's head (and/or any other anatomical region having target neurons for stimulation) such that each of the magnetic stimulators span a separate region of the head. FIGS. 1A-1C depict one variation where the magnetic neural stimulation system 100 is positioned such that the first magnetic stimulator 102 covers a first region of the head 106 and the second magnetic stimulator 104 cover a second region of the 108 that is different from the first region 106. In some variations, the first and second regions 106, 108 may have overlapping portions while in other variations, the first and second regions 106, 108 may not overlap at all. The stimulators may be positioned at a distance from the tissue, where the selected distance may help to reduce heating of the superficial tissue surface. For example, the stimulators 102, 104 may be placed 5 mm from the scalp of the head, and as depicted in FIG. 1C, each stimulator may be positioned at an angle PA with respect to an axis that is parallel to a tangent of the tissue surface. For example, the angle PA may be from about 0 degrees to about 60 degrees, e.g., about 15 degrees.

The helically coiled stimulators may be enclosed in a cast. For example, as depicted in FIG. 1D, the magnetic stimulators 102, 104 may be enclosed in a bi-cylindrical cast 116, where each cylindrical region encompasses one stimulator. The cast 116 may be made of any insulating material that does not substantially interfere with the magnetic field induced by the stimulators, for example, ABS, HDPE or Teflon. There may be a space between the stimulators and the interior wall of the cast, which may allow air to be circulated within the case 116 to cool the stimulators, if needed.

FIGS. 2A-2D depict a top view (X-Y plane) of a helically coiled stimulator having a star polygon profile and one method of making such an stimulator. The stimulator 200 may have a first end 202 that may be a positive terminal and/or current source, and a second end 204 that may be a negative terminal and/or current sink. The first end 202 may be located along the central axis of the coil (which extends into the page). The coil 200 may be formed by bending a single wire such that each acute turn of the coil is located at the (X, Y, Z) coordinates listed in the table shown in FIG. 2D. The first end 202 may start at point-a having coordinates (0, 0, 0), extend 10.4 mm to the left to a first bend at point-b having coordinates (−10.4, 0, 0), which is the first point that is part of the coil structure. The wire then extends to point-c having coordinates (0, 40, 0), which may be the first turn of the helical coil, where the angle of the turn is 30 degrees. Next, the wire extends to point-d having coordinates (20, −34.64, 1), which is the second turn of the helical coil having a rise of about 1 mm per turn (e.g., for a wire with a diameter of 1 mm). The rise may vary depending on the diameter of the wire, and the amount of space desired for the air circulation (e.g., for cooling purposes). Each turn of the helical is formed stepwise as provided in the table of FIG. 2D. The second end 204 may also be aligned along the central axis of the coil, but offset from the first end 202 in the z-direction by 12 mm. The second end 204 may be connected to a negative terminal of a high voltage generator or may be connected to the first end of a second stimulator of a magnetic neural stimulation system. The wire diameter may vary according to the maximum level of current that is to be supplied to the wire.

Figure 3A:
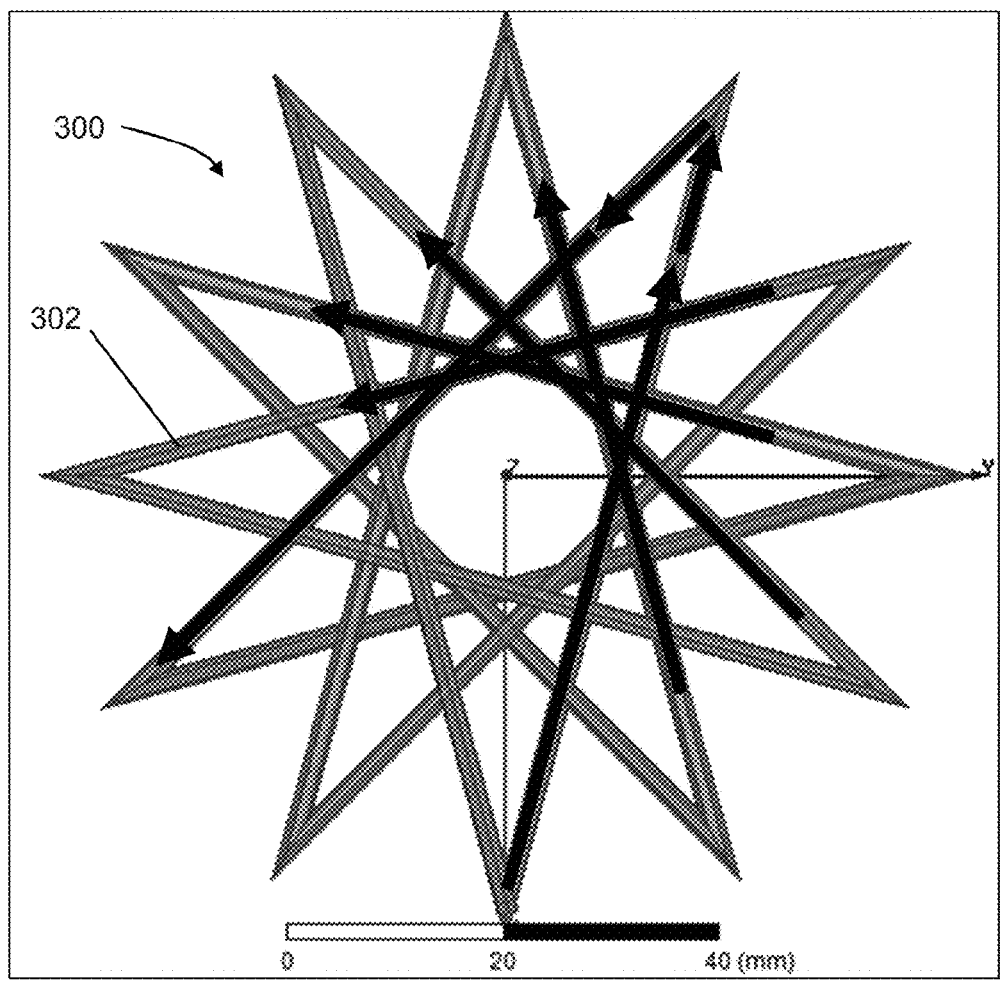
FIG. 3A schematically depicts a subset of the current flow through the single wire of a ramped or helically coiled stimulator.
Figure 3B:
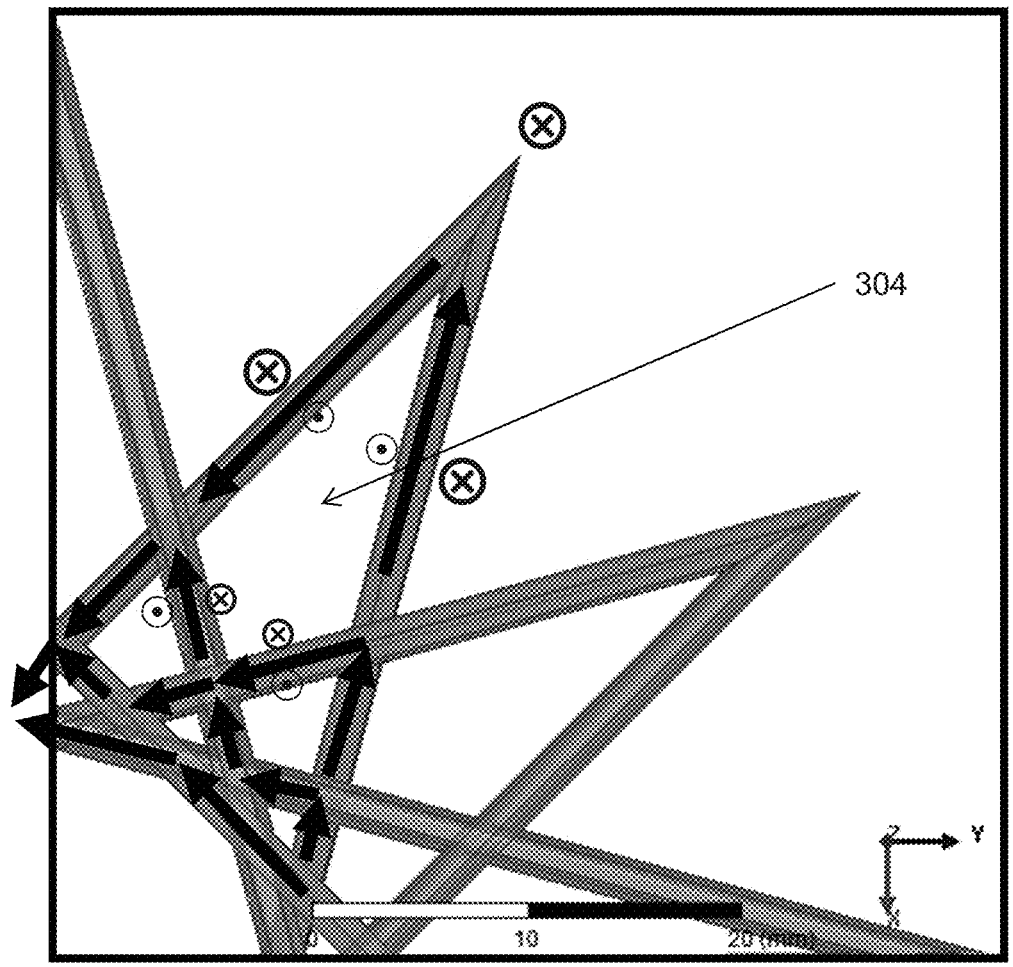
FIGS. 3B-3E depict close-up views of the current flowing through wire crossings at various regions of the ramped or helically coiled stimulator, and the direction of the magnetic field lines induced by the current.
Figure 3C:
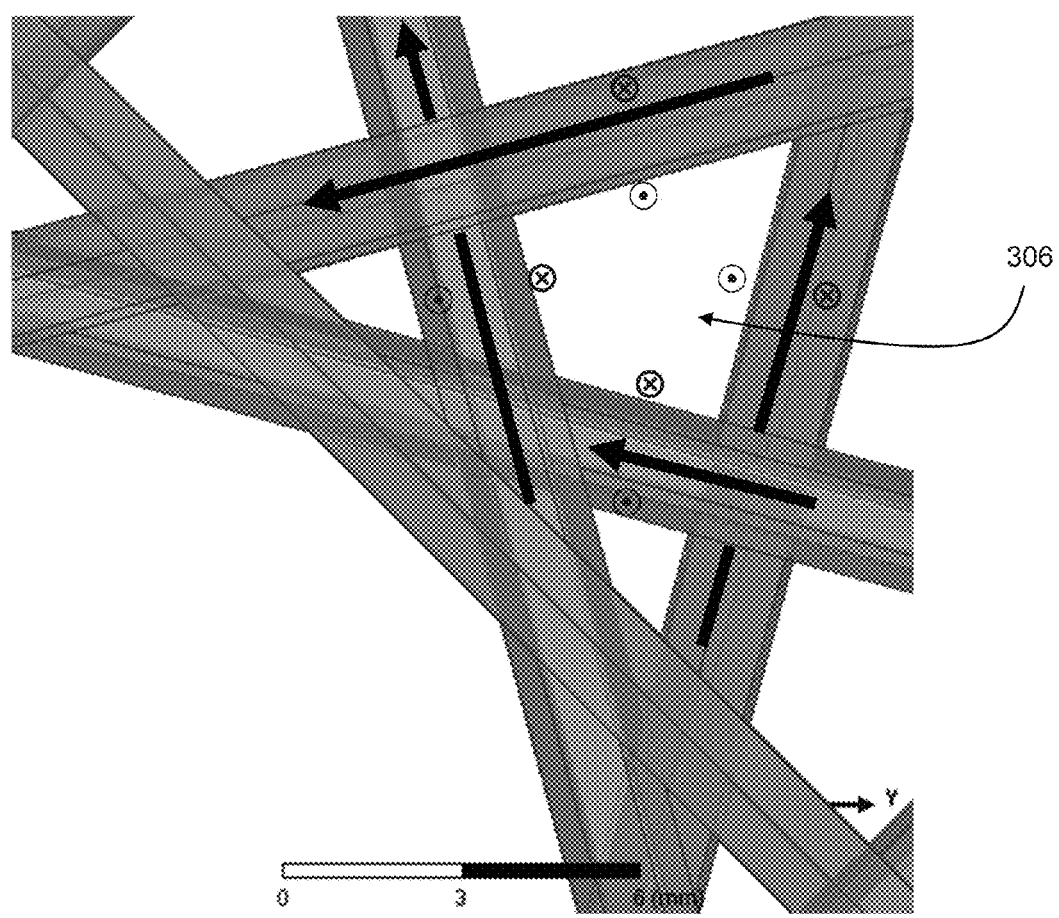
Figure 3D:
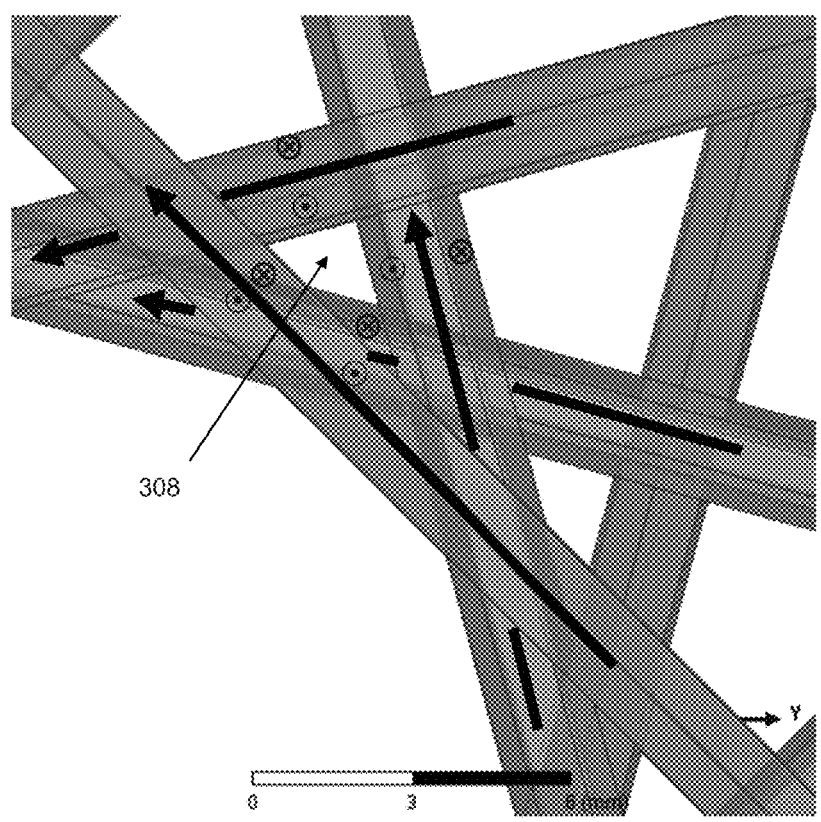
Figure 3E:
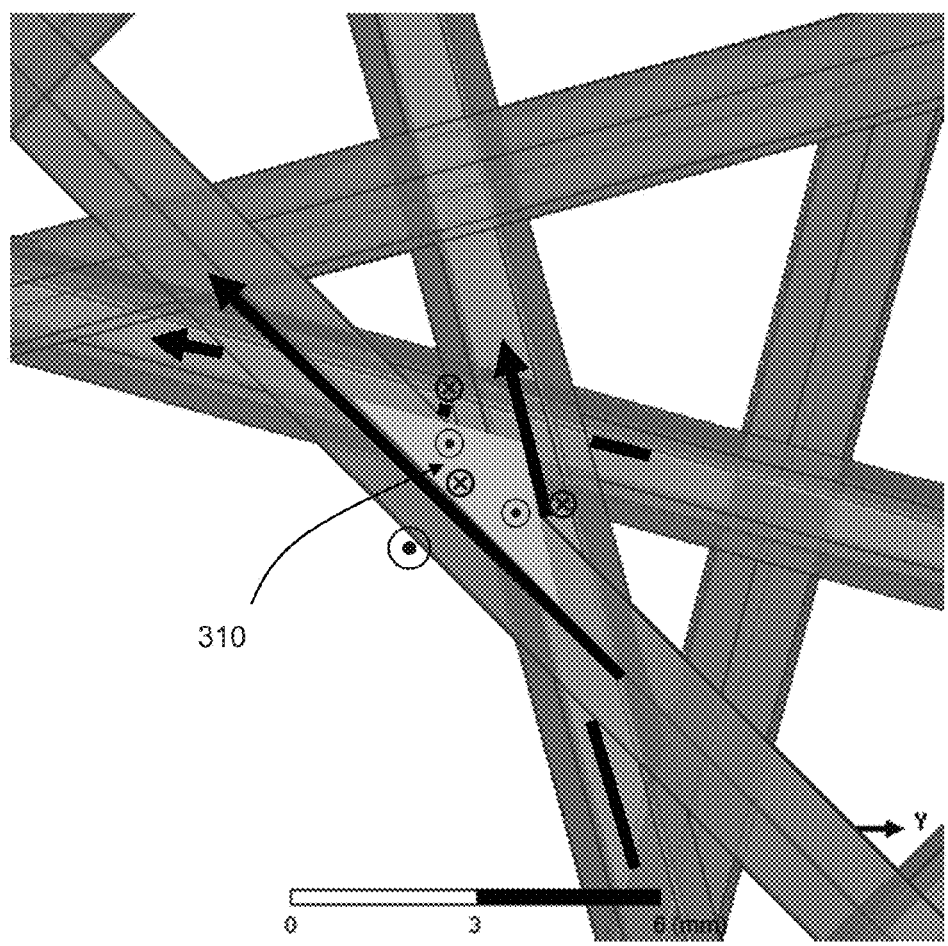
Figure 3F:
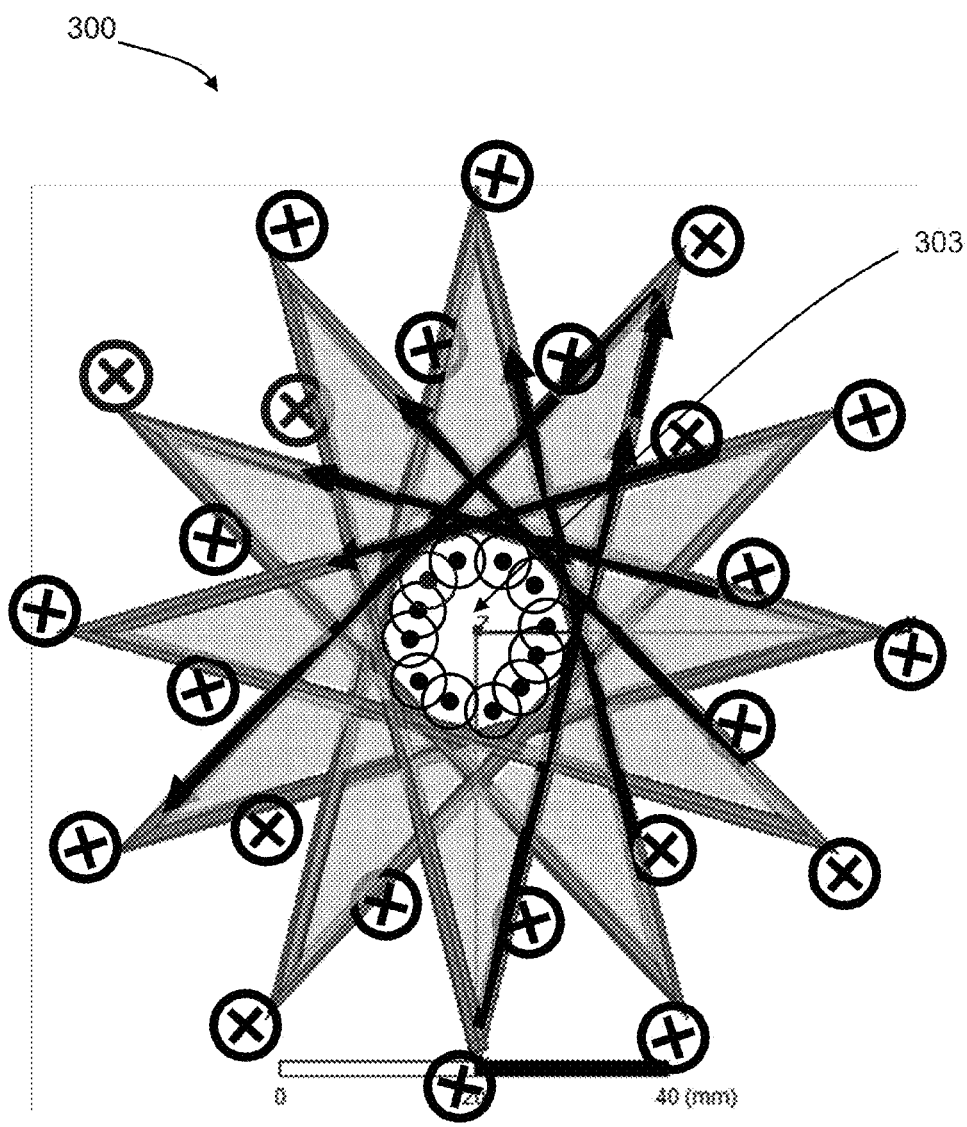
FIG. 3F schematically depicts the cumulative direction of the magnetic field lines induced by a current through the single wire of a ramped or helically coiled stimulator.
Figure 3G:
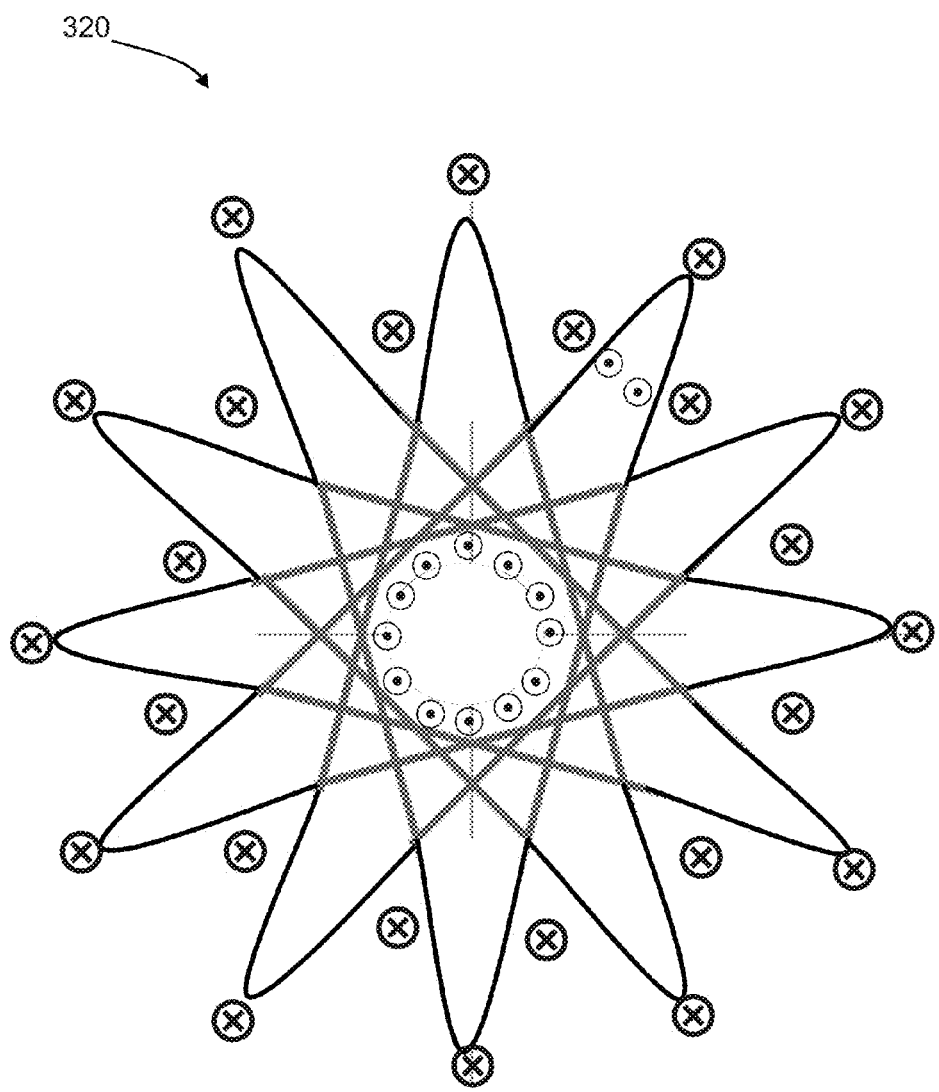
FIG. 3G schematically depicts the cumulative direction of the magnetic field lines induced by a current through the single wire of a ramped or helically coiled stimulator with a plurality of acute turns that are curved.

The eddy currents induced by a magnetic field induced by a current that is provided to a helically coiled stimulator may be distributed such that deeper tissue structures may be magnetically stimulated without heating the superficial tissue structures to the same degree as a non-helically coiled stimulator would. Without being bound by theory, the acute turns of the helically coiled stimulator and the central region with a high density of overlapping segments of the same wire may act to "repel" the magnetic field lines further away from the stimulator, which would allow it to induce eddy currents at deeper tissue structures more efficiently than a magnetic stimulator without acute turns (e.g., a Figure-eight stimulator). FIGS. 3A-3F schematically depict the direction of the current (dark lines) through the single wire 302 of a helically coiled stimulator 300 with 12 acute turns. FIG. 3B is a close-up view of a region 304 of the helically coiled stimulator 300. Although the current through the wire 302 is uniform throughout the wire 302, direction of the current in the wire crossings that surround the region 304 may generate magnetic field lines with opposing directions that cumulatively give rise to stronger magnetic field outside of the region 304 than inside of the region 304. The direction of the magnetic field lines induced by the currents in the wire crossings around the region 304 is represented by a circle with a central dot to indicate field lines pointing up out of the page and a circle with a cross to indicate field lines pointing down into the page. As depicted in FIG. 3B, the field lines within the region 304 oppose each other, but the field lines outside of the coil all point down into the page. More generally, as depicted in FIGS. 3C-3E, internal regions 306, 308, 310 bounded by the multiple crossings of the single wire in the central mesh region generate magnetic field lines with opposing directions. However, as depicted in FIG. 3F, the regions outside of the helically coiled stimulator (e.g., regions that are not bound by multiple wire crossings) have magnetic field lines that all have the same direction (i.e., going downward into the page), while the central opening 303 has magnetic field lines that all have the same direction, but opposite to the field lines outside of the coil (i.e., going upward out of the page). Similar magnetic field lines may be induced by a helically coiled stimulator 320 with curved turns, as depicted in FIG. 3G. Such distribution of unidirectional field lines outside the helically coiled stimulator and in the central opening of the stimulator may enhance the magnitude of the field lines such that they penetrate more deeply into the tissue. Because a helically coiled stimulator with multiple acute turns can stimulate deeper tissues with less current than a magnetic stimulator without acute turns, superficial tissue (e.g., scalp, surface skin) may not be subject to as much heat as compared to using a non-helically coiled stimulator to obtain similar levels of stimulation. Since the heat experienced by superficial tissue structures may be reduced, any pain or discomfort experienced by the patient may also be similarly reduced. In addition, this may allow for prolonged or repetitive stimulation, e.g., r-TMS. This may be particularly useful for treatment of depression.

Figures 4A, 4B, 4C:
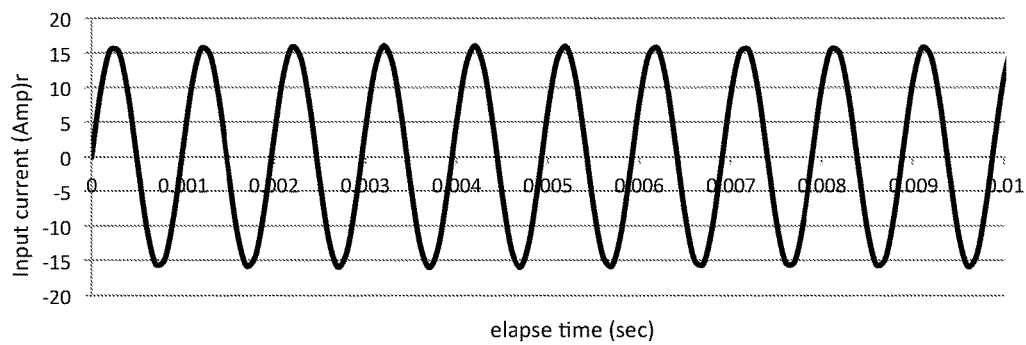
FIGS. 4A-4C depict simulation parameters used to model the eddy current density profile generated by a ramped or helically coiled stimulator as compared to a Figure-eight stimulator.
Figure 4D:
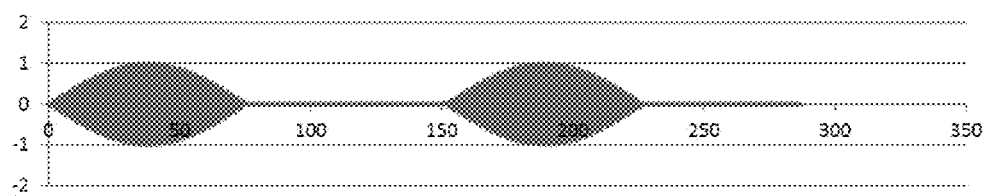
FIG. 4D depicts one variation of an input current waveform that may be used in stimulation.
Figure 4E:
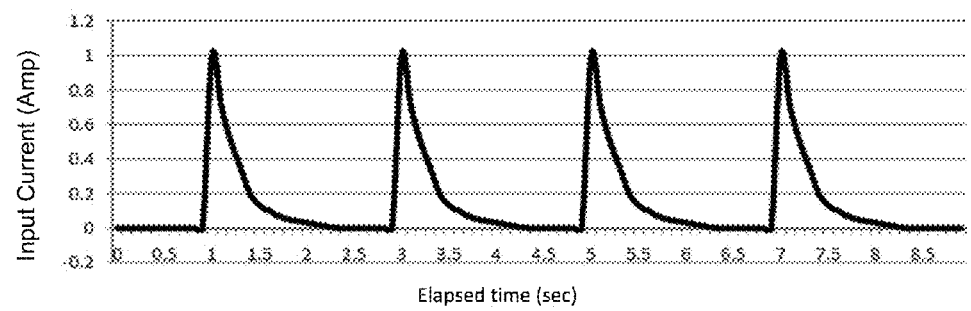
FIG. 4E depicts another variation of an input current waveform that may be used in stimulation.
Figure 5A:
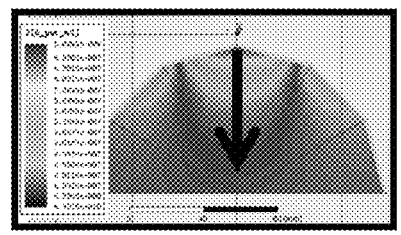
FIGS. 5A-5D depict the simulation results using the parameters of FIGS. 4A-4C.
Figure 5B:
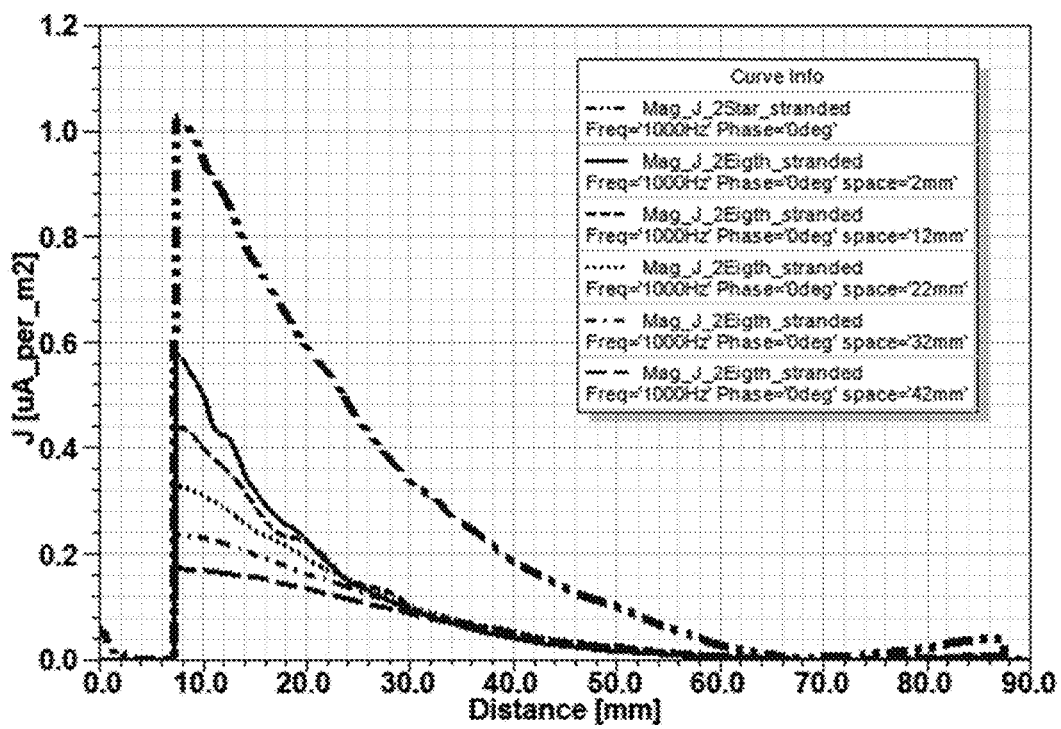
Figure 5C:
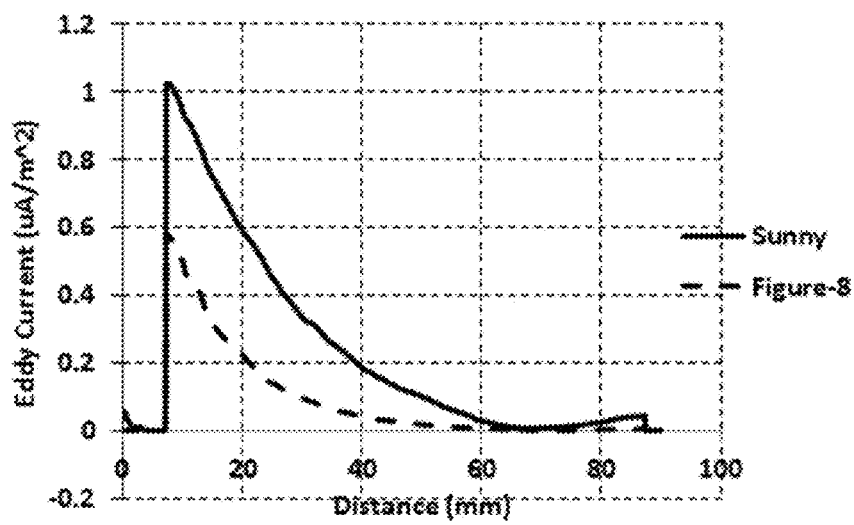
Figure 5D:
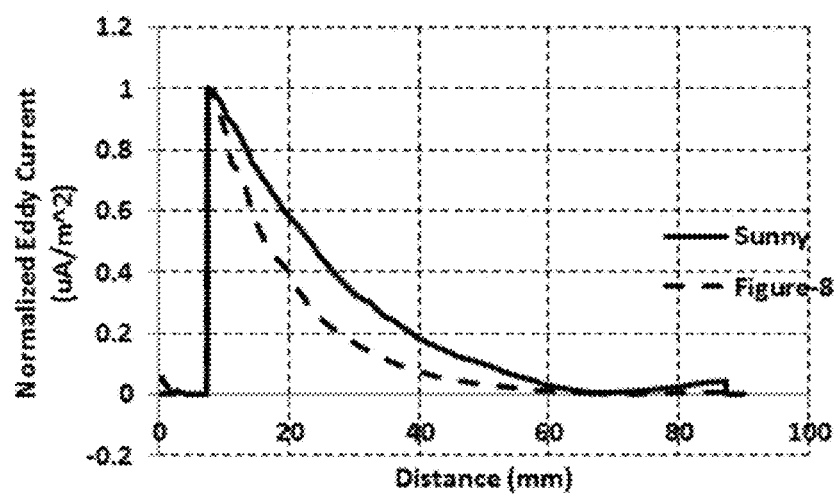

The eddy currents induced by a magnetic field generated by a current that is provided to a helically coiled stimulator may be modeled using the parameter values and stimulation waveform depicted in FIGS. 4A-4D. The distribution eddy currents of helically coiled stimulators and Figure-eight stimulators were modeled for comparison. The helically coiled stimulators, Figure-eight stimulators, human head models and the eddy current solver were implemented with the finite element method based on Maxwell's equations. The human head was modeled by a semi-spherical shape with a 16 cm diameter, where the outer portion of the sphere was modeled as cortical bone of the skull having a thickness of 7 mm with the parameter values outlined in the table of FIG. 4A, and the inner portion of the sphere (e.g., brain matter) was modeled with the parameter values outlined in the table of FIG. 4B. The values associated with human tissue properties and parameters may be based on data published by the Italian Research Council (http://niremf.ifac.cnr.ithissprop/htmlclie/htmlclie.htm#atsftag). The eddy currents induced by a pair of helically coiled stimulators (the stimulators described and depicted in FIGS. 1A-1E) and Figure-eight stimulators were modeled. The current applied to the stimulators was a sine wave, having a frequency of 1 kHz and a magnitude of 16 A, as depicted in FIG. 4C. In other simulations, it is possible to provide an input current having any frequency, for example a frequency less than 1 Hz (which may provide excitatory stimulation to neurons) or a frequency equal to or greater than 1 Hz (which may inhibit neuronal activity). Input current waveforms may include various sinusoidal waveforms (such as the waveform depicted in FIG. 4D), square waveforms, decaying peak waveforms (such as the waveform depicted in FIG. 4E) and may be pulsed or continuous. The input current may be bipolar or unipolar. Other examples of potential input waveforms are described in various research papers, including a paper by Zhi-De Deng et al 2011 J. Neural Eng. 8 016007 doi:10.1088/1741-2560/8/1/016007. The positions of the helically coiled stimulators and Figure-eight stimulators were kept the same, and had the same positions as shown in FIG. 1B. For some simulations, the spacing between the individual loops of the Figure-eight stimulator was varied, from 2 mm to 42 mm FIG. 5A depicts an example of the simulated eddy current density distribution. The arrow indicates the axis along which the magnitude of the eddy current density is measured to for FIGS. 5B-5D. The plot of FIG. 5B compares the eddy current density of both the helically coiled stimulators and Figure-eight stimulators as a function of distance from the surface of the head into the white matter of the brain. The distance is measured at the midline of the head, as indicated by the arrow. As shown there, the eddy currents induced by the helically coiled stimulators is greater at higher distances than the eddy currents induced by the Figure-eight stimulators, regardless of the spacing between the loops of the Figure-eight stimulators. The depth of penetration of the eddy currents induced by the helically coiled stimulators is greater than the penetration depth of the eddy currents induced by the Figure-eight stimulators. In addition, the helically coiled stimulator may give rise to an eddy current density near the surface of brain's white matter that is about twice current density as would be provided by a Figure-eight stimulator. FIG. 5C depicts a plot of the eddy current density as a function of distance for helically coiled stimulators and the best of Figure-eight stimulators (with 2 mm spacing), and FIG. 5D depicts a plot of the normalized eddy current density (i.e., eddy current density is normalized to the maximum eddy current density value at the surface of the head model) in the white matter of the head model. The solid line represents the eddy current density generated by a helically coiled stimulator and the dotted line represents the eddy current density generated by a Figure-eight stimulator. As may be seen there, with the same amount of current applied to each of the stimulators, the magnitude of the eddy current density induced by the helically coiled stimulator is greater at a deeper distance into the white matter of the head model as compared to the eddy current density induced by the Figure-eight stimulator. These simulation results indicate that with the same amount of current applied to the helically coiled stimulator and the Figure-eight stimulator, the stimulation strength and depth of penetration is greater for the helically coiled stimulator than for the Figure-eight stimulator.

Figure 6:
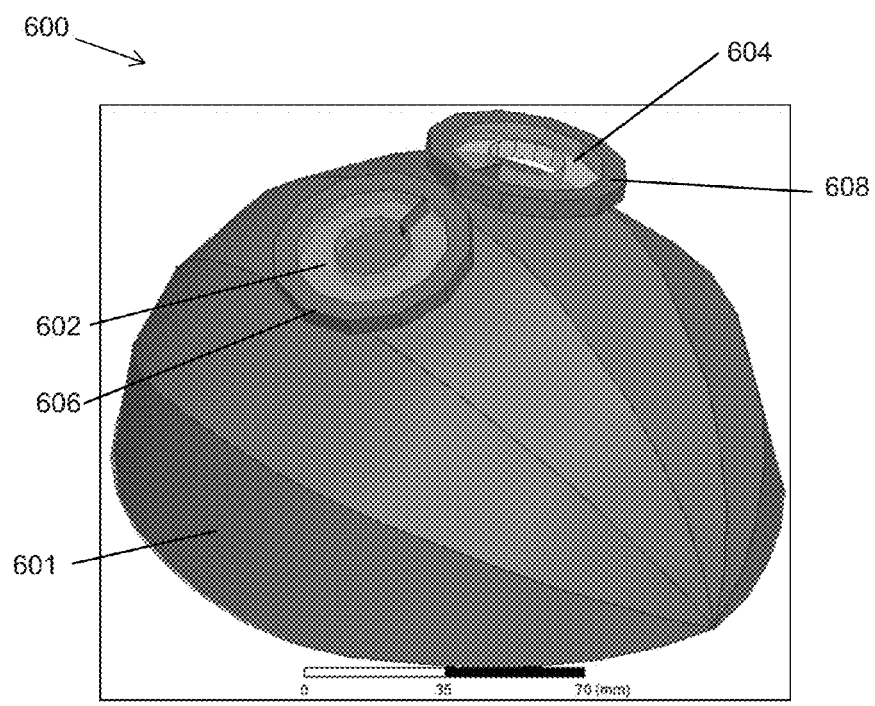
FIG. 6 depicts another of a magnetic stimulator.

Another variation of a magnetic stimulator is depicted in FIG. 6. The stimulator 600 may comprise a first wire loop 602, a second wire loop 604, a first magnetic ring 606 circumscribing the first wire loop 602 and a second magnetic ring 608 circumscribing the second wire loop 602. The first and second magnetic rings may be permanent magnets, and may be made of any magnetic material, such as iron, nickel, cobalt, and may include alloys (e.g., a neodymium-iron-boron alloy). The loops of the stimulator 600 may be located adjacent to each other and coupled together via a connector, and in some examples, may be substantially co-planar. A connector between the first and second loops may allow the angle between the two loops to be adjusted. For example, the angle between the first and second loops 602, 604 of the looped stimulator 600 may be adjusted to approximate the radius of curvature of a head 601. Without being bound by theory, the magnetic rings around the wire loops may act to "repel" the magnetic field lines of the wire loops when a current is provided through the loops such that the field lines extend further in a direction orthogonal to the plane of the loops (i.e., in the z-direction). This may allow the looped stimulator to generate a magnetic field that penetrates deeper into the tissue than a similar looped stimulator without magnetic rings. As a result, a looped stimulator with magnetic rings may induce eddy currents at a deeper tissue depth than a looped stimulator without magnetic rings.

Figure 7:
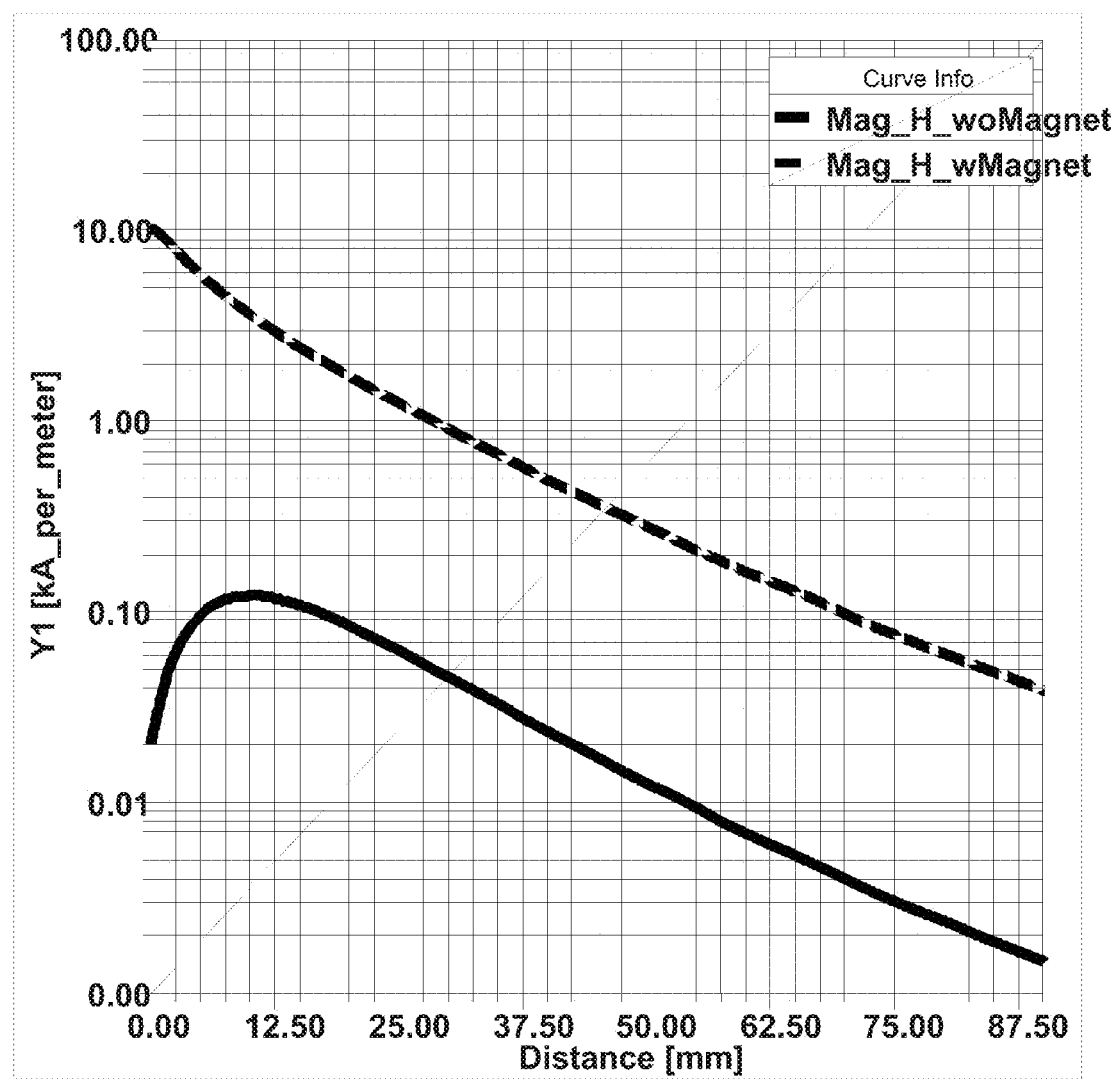
FIG. 7 plots the eddy current density generated by a looped stimulator with permanent magnet rings as compared to a Figure-eight stimulator without magnet rings.

The eddy currents induced by the looped stimulator and the Figure-eight stimulator have been modeled using similar parameters as previously described and detailed in FIGS. 4A-4C, and include additional parameters to model the magnetic characteristics of the magnetic rings. For example, simulations were run on a looped stimulator with neodymium-iron-boron magnetic rings that have the following characteristics: relative permittivity of 1, relative permeability of 1, conductivity of 7.14e+5 s/m, dielectric loss tangent of 0 (zero), magnetic loss tangent of 0 (zero), and magnetic coercivity of 1.00e+6 A/m. The results of those simulations are depicted in FIG. 7. FIG. 7 depicts a plot that compares the eddy current density as a function of distance for the looped stimulator of FIG. 6 (which has magnetic rings) and a Figure-eight stimulator (which lacks magnetic rings). As depicted there, the current density attained by using the looped stimulator is about ten times the current density attained by using a Figure-eight stimulator. The magnetic rings of the looped stimulator may act to "amplify" the amount of electric field that is induced by the wire loops such that the eddy currents are greater than if they were generated by a Figure-eight stimulator that does not have the magnetic rings.

Figure 8A:
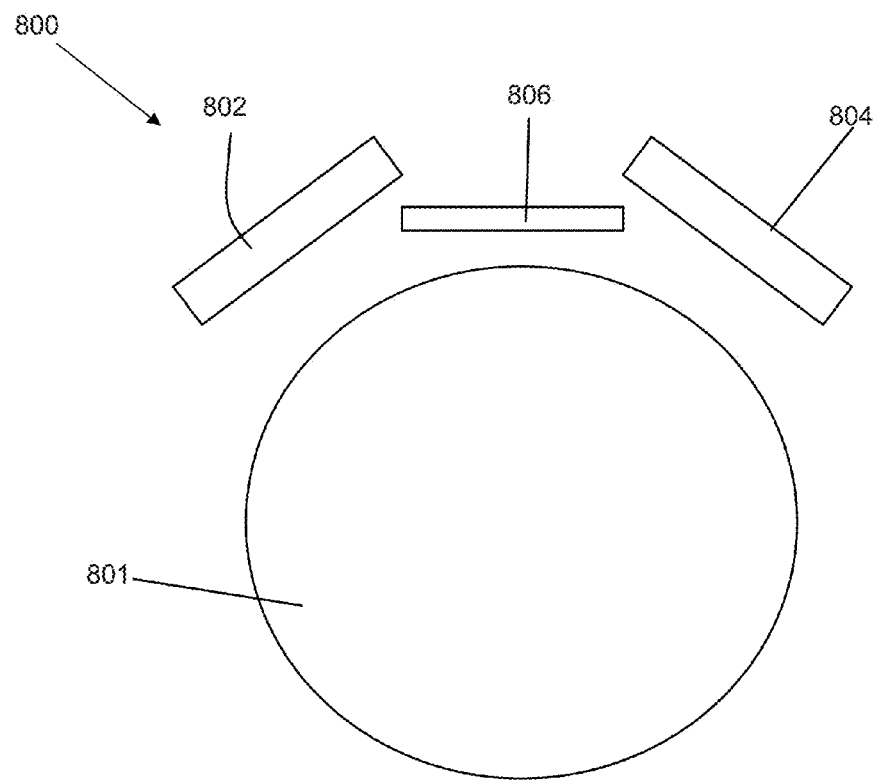
FIG. 8A depicts one variation of a magnetic neural stimulation system comprising one or more stimulators and a shielding component.
Figure 8B:
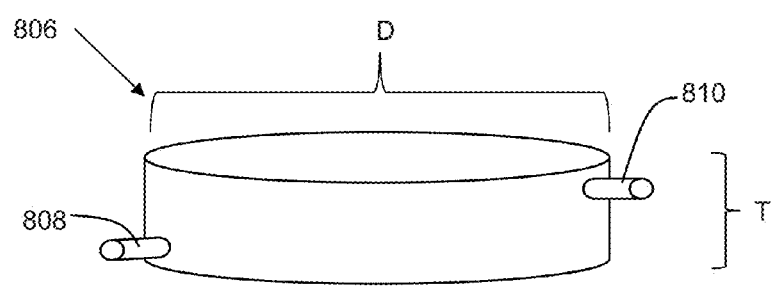
FIG. 8B depicts one variation of a shielding component.
Figure 10E:
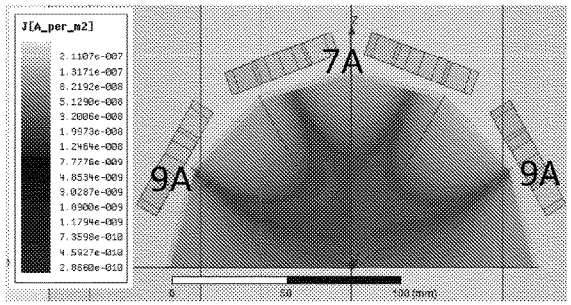
FIG. 10 depict graphs including the simulation results using the parameters of FIG. 9 of the eddy current density profile generated by an array of Figure-eight stimulators with various stimulation currents and without shielding components.
Figure 10G:
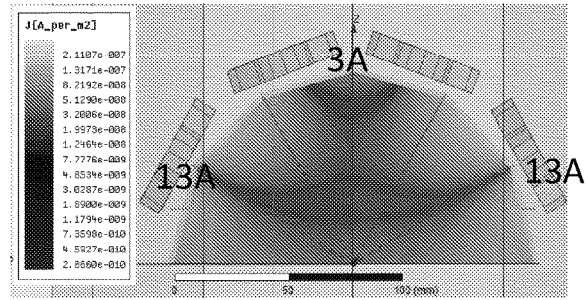
Figure 10F:
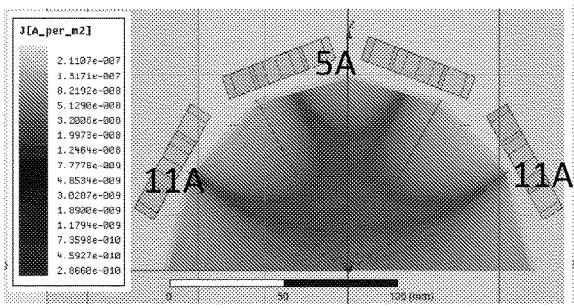
Figure 10H:
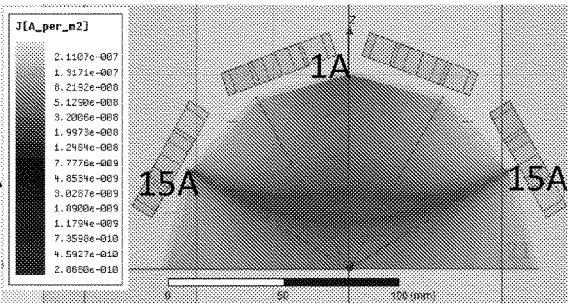
Figures 11A, 11C:
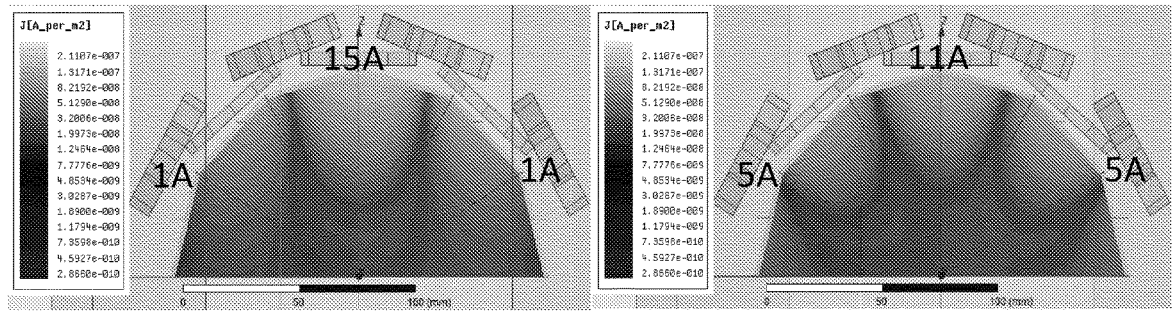
FIG. 11 depict graphs including the simulation results using the parameters of FIG. 9 of the eddy current density profile generated by an array of Figure-eight stimulators with various stimulation currents and with shielding components.
Figures 11B, 11D:
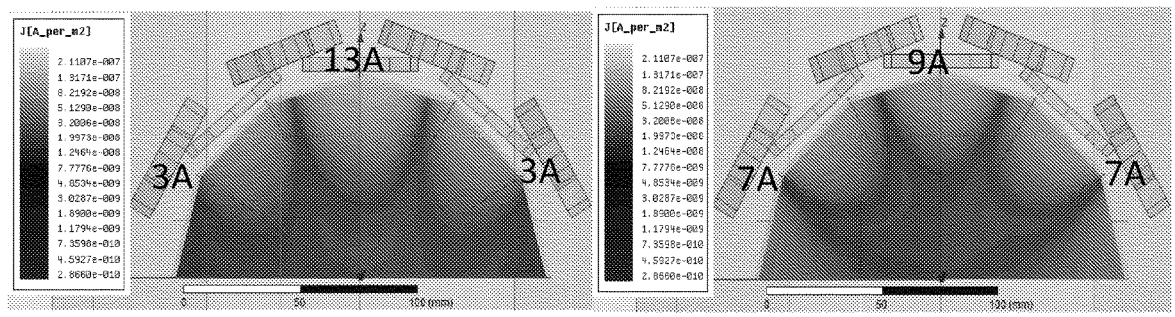
Figures 11E, 11G:
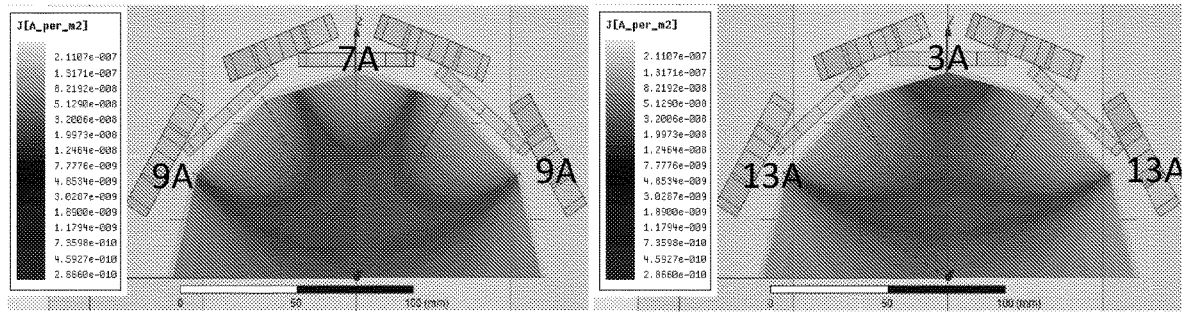
Figures 11F, 11H:
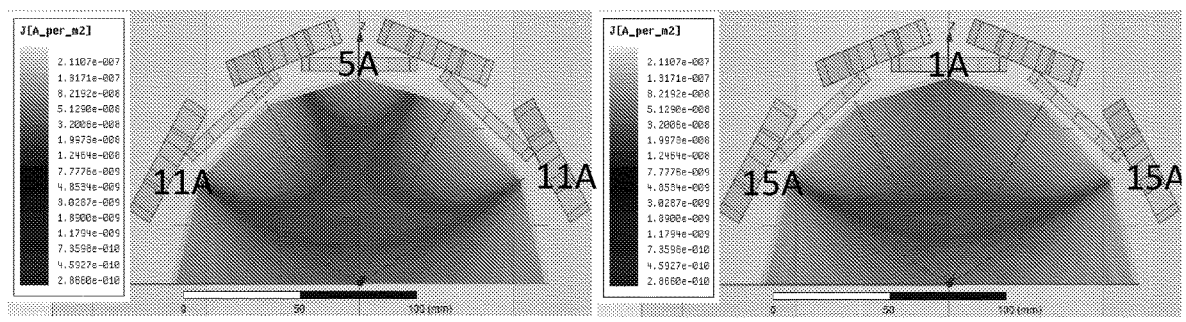

Optionally, some variations of a magnetic neural stimulation system may also comprise one or more magnetic shielding components, which may be placed between the magnetic stimulators. For example, a magnetic neural stimulation system may comprise a plurality of magnetic stimulators that are spaced apart from each other (e.g., the magnetic stimulators may be in an array such that they do not overlap each other). The magnetic stimulators may be any of the magnetic stimulators described herein. One or more shielding components may be located in the spaces between the magnetic stimulators. The shielding component may be used to reduce the sensation of pain experienced by the patient that may arise from the eddy currents induced by the stimulators when they are activated. The shielding component may also shape the magnetic field generated by the stimulators so that the density of induced eddy currents are reduced in the superficial tissue structures. Inducing eddy currents in superficial tissue structure (or any non-target tissue in general) may cause pain and seizures in some patients, which may result in the interruption or termination of treatment for those patients. FIG. 8A schematically depicts a magnetic neural stimulation system 800 disposed over a head model 801, the system comprising a first stimulator 802, a second stimulator 804 adjacent to the first stimulator, and a shielding component 806 between them. In one variation, the shielding component 806 may be a cylindrical disc, as depicted in FIG. 8B. The cylindrical shield 806 may have a diameter D of about 50 mm and a thickness T of about 5 mm. The cylindrical shield 806 may be configured to retain a fluid, such as saline, which may help to dissipate heat generated by the stimulators during use and may also modulate the magnetic field generated by the stimulator. The fluid may be circulated through the cylindrical shield, for example, via inlet and outlet channels 808, 810.

The effect of including one or more shielding components in a stimulation system on the density and distribution of induced eddy currents was simulated using similar parameters and models as described previously. In the simulations, the fluid within the shielding component was modeled as saline, with the parameters outlined in the table of FIG. 9. The simulation results in the plots of FIG. 10, including a-h graphs and FIG. 11, including a-h graphs and summarized in FIG. 12 reflect the density and distribution of eddy currents induced by four Figure-eight stimulators and three cylindrical shields disposed between the stimulators positioned over a head. The amount of current applied across each stimulator is indicated in each of the plots. For example, to obtain the simulated eddy current distribution depicted in graph a of FIGS. 10 and 11, 15 A of current was applied to the middle two stimulators, and 1 A was applied to each of the side stimulators. Graph a of FIG. 10 shows the eddy current distribution generated by four stimulators without shielding components, while graph a of FIG. 11 shows the eddy current distribution of the same four stimulators but with a cylindrical shielding component disposed between each of the stimulators. To obtain the simulated eddy current distribution depicted in graph h of FIGS. 10 and 11, 1 A of current was applied to the middle two stimulators, and 15 A was applied to each of the side stimulators. Graph h of FIG. 10 shows the eddy current distribution generated by four stimulators without shielding components, graph h in FIG. 11 shows the eddy current distribution of the same four stimulators but with a cylindrical shielding component disposed between each of the stimulators. The normalized eddy current density at various locations along the surface of the head (e.g., at the central axis of the head, 30 degrees from a central axis of the head, 60 degrees from the central axis of the head) is summarized in the table depicted in FIG. 12. The numbers reflected in the table are the eddy current density at the head surface normalized to eddy current density 2.5 cm deep within the head. With cylindrical shields between each of the stimulators, the eddy current density along the surface of the head is reduced. For example, the normalized eddy current density on the head surface at the central axis based on the current simulation pattern of graphs a of FIGS. 10, 11 is without shielding is 2.97 and 2.58 with shielding. As depicted in the plots of FIGS. 10 and 11, and the summary table of FIG. 12, adjusting the magnitude of the current through the stimulators and the location and angle of the stimulators with respect to the head may modulate the profile of the induced eddy current. In combination with shielding components, specific eddy current distribution profiles (e.g., shape, density, depth, etc.) may be obtained. These may allow a practitioner to selectively stimulate targeted neural populations in the brain, while reducing stimulation of non-target neurons. Selectively stimulating neural populations in brain while avoiding or reducing stimulation of non-targeted neurons may help to reduce the amount of pain experienced by the patient (e.g., scalp pain, discomfort from heat from the stimulator), which may allow for prolonged and/or repeated stimulation treatment.

Figure 13A:
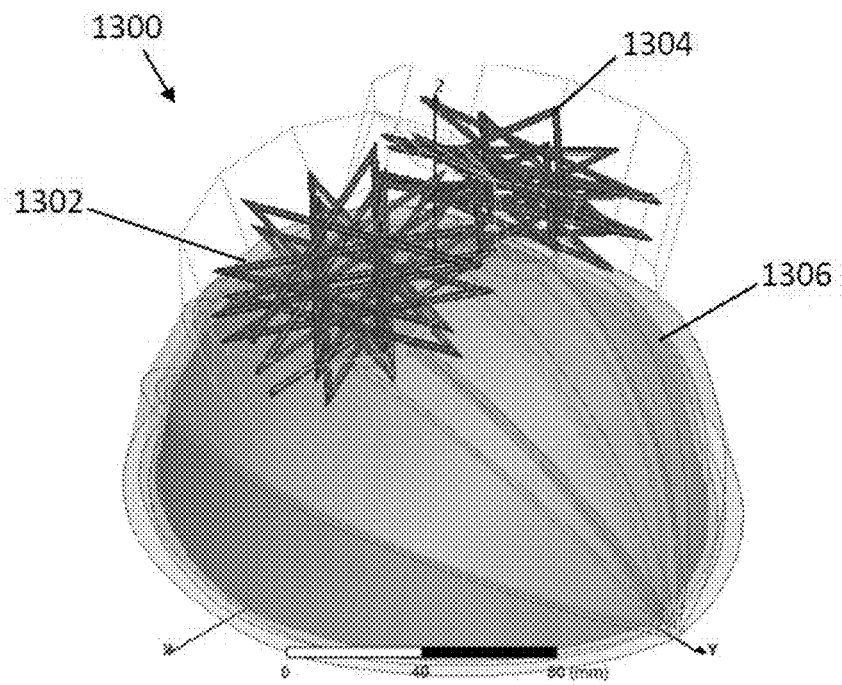
FIGS. 13A-13C depict one variation of a magnetic stimulation system comprising at least one magnetic stimulator and a shield.
Figure 13B:
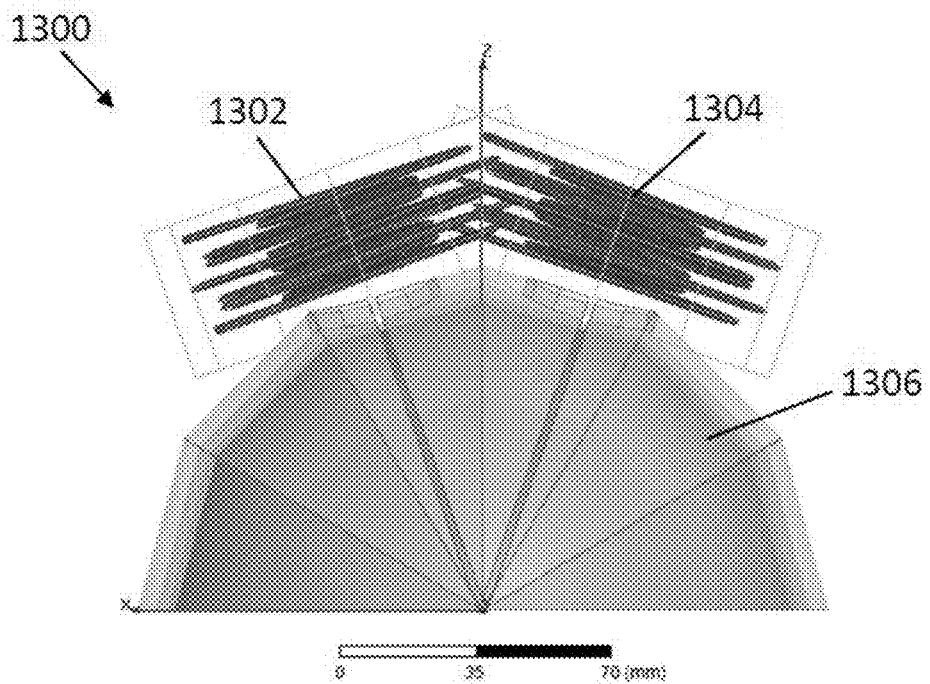
Figure 13C:
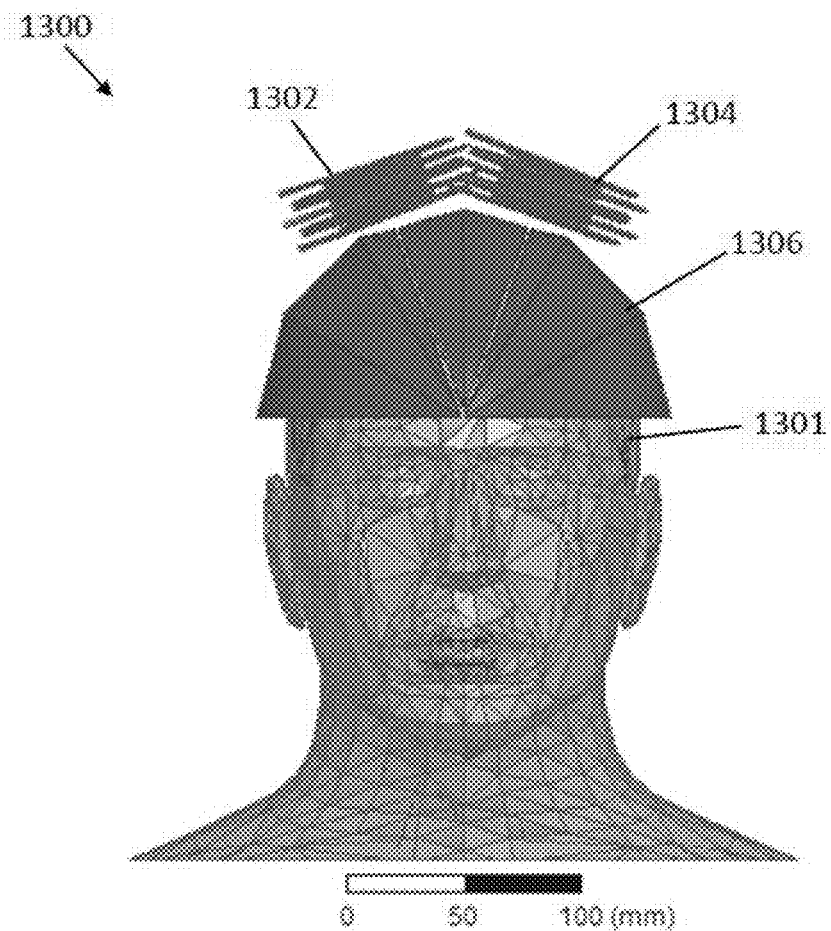
Figure 14A:
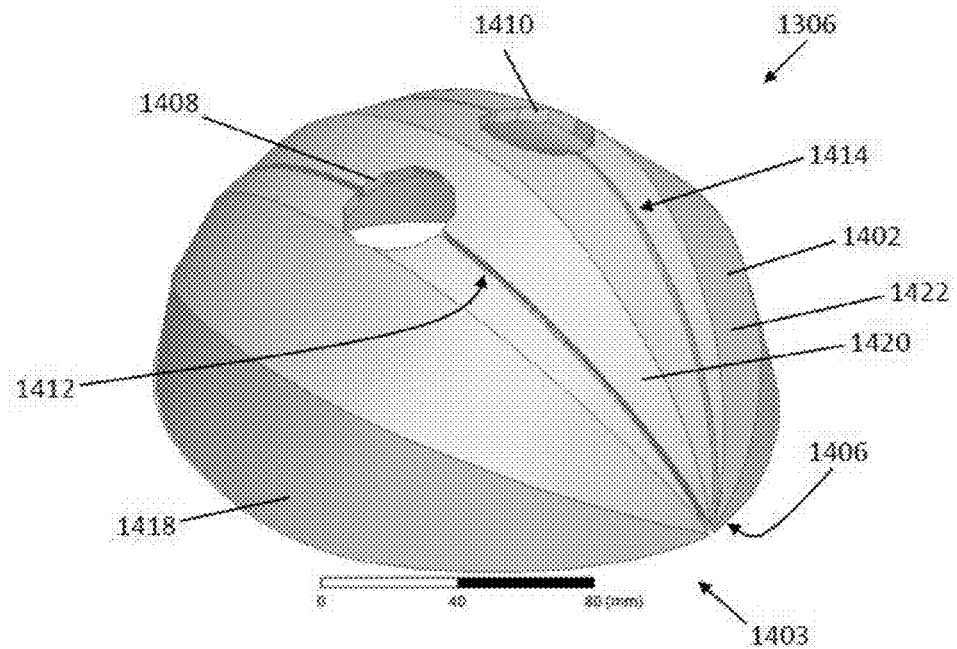
FIG. 14A is a perspective view of one variation of a shield.
Figure 14B:
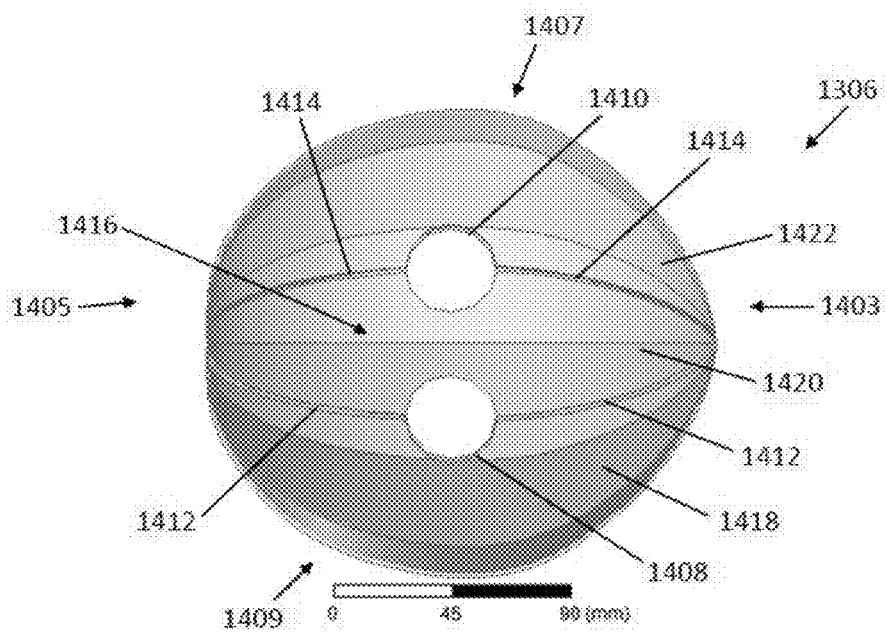
FIG. 14B is a top view of the shield of FIG. 14A.
Figure 14C:
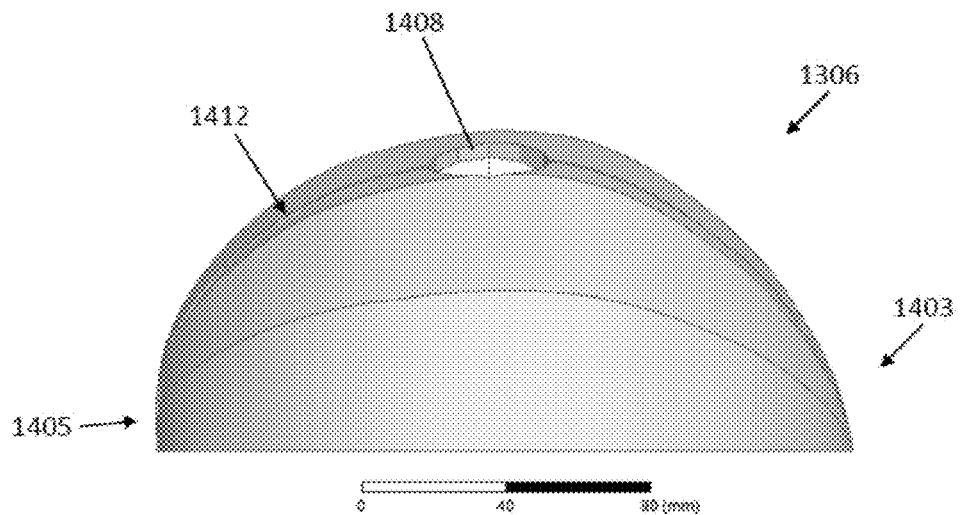
FIG. 14C is a side view of the shield of FIG. 14A.
Figure 14D:
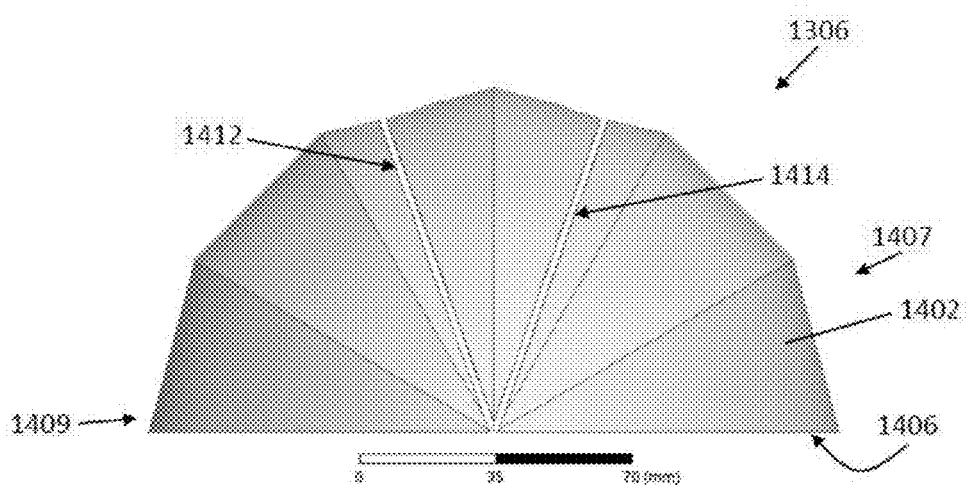
FIG. 14D is a front view of the shield of FIG. 14A.

Another variation of a magnetic shield that may be used with any of the magnetic stimulators described herein is depicted in FIGS. 13A-13C. Magnetic stimulation system 1300 may comprise a first stimulator 1302, a second stimulator 1304, and a shield 1306. The first and second stimulators 1302, 1304 may be arranged to be adjacent to each other (e.g., connected to each other in series) and positioned over a patient's head 1301, with the shield 1306 located between the stimulators and the patient's head. The shield 1306 may be sized and shaped to fit over a patient's head (or any anatomical region for which magnetic stimulation and/or shielding is desired). Additional views of the shield 1306 are depicted in FIGS. 14A-14D. As illustrated there, shield 1306 may comprise an external surface 1402, an internal surface 1406, an enclosed internal cavity that extends between the external and internal surfaces, a first opening 1408, a second opening 1410, a first channel 1412 that intersects the first opening 1408 and extends between the front 1403 and back 1405 of the shield 1306, and a second channel 1414 that intersects the second opening 1410 and extends between the front 1403 and back 1405 of the shield 1306. The external surface is the side of the shield that may be closest to the stimulators and the internal surface is the side of the shield that may be closest to the skin surface (e.g., may contact the skin surface). The first and second openings 1408, 1410 and the first and second channels 1412, 1414 may transect and/or extend through the entire thickness of the shield 1306. The internal cavity of the shield may be filled with a conductive fluid (e.g., saline, salt water, sulfuric acid solutions containing iron oxide nanocrystal particles, etc.), which may act as a thermal sink and/or medium in which eddy currents may be induced. The external and internal surfaces of the shield may be made of a non-conductive material and may optionally be transparent or translucent. The openings may allow the magnetic field from the stimulators pass through into the tissue underneath the shield, while the tissue located under the shield in the space between the first and second openings may be shielded from magnetic stimulation such that the induced eddy current density in that region is less than what the eddy current density would be if the shield was absent. In some variations, the shield may comprise a hollow walled structure with one or more openings that extend through the wall and a conductive fluid within the hollow portion of the wall. The stimulator structures described herein may also be used alone, without shield, or may be used with other magnetic or temperature shielding known in the art. The shielding described herein may also be used with other types of stimulators known in the art.

Figure 15A:
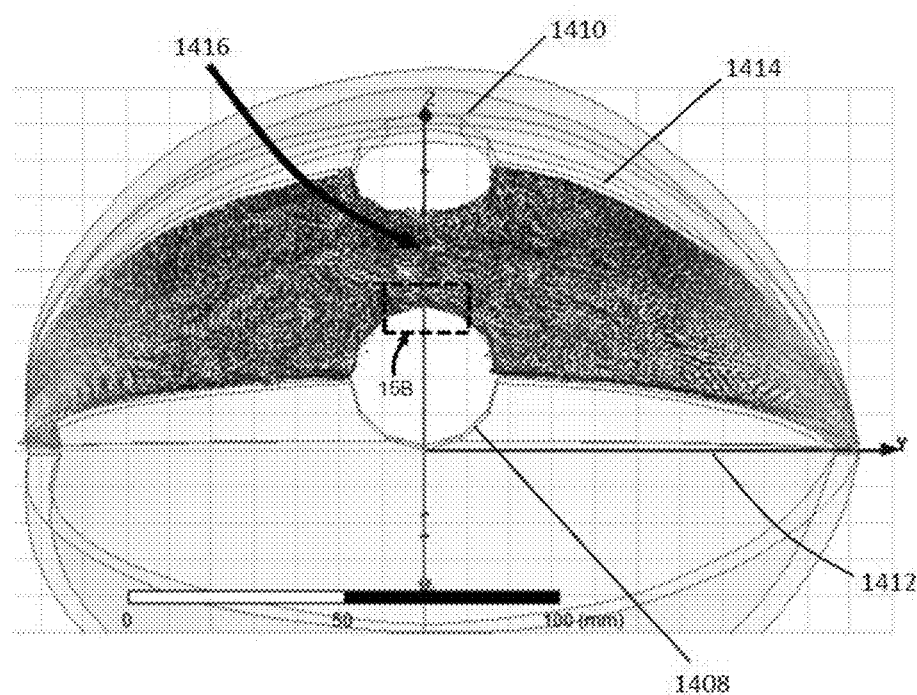
FIG. 15A depicts a simulation of the eddy currents that may be induced in a portion of a shield during magnetic stimulation.
Figure 15B:
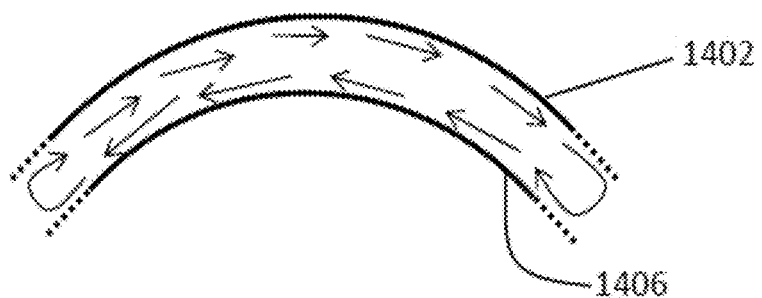
FIG. 15B is an inset of a portion of FIG. 15A depicting a schematic cross-sectional diagram of the direction of eddy current flow.

The shield 1306 may be capable of reducing the induced eddy current density of surface tissue that is located under the shield between the first opening 1408 and the second opening 1410. The magnetic field applied by the first and second stimulators 1302, 1304 may pass through the first and second openings 1408, 1410 without significant attenuation from the shield 1306, but may be attenuated by the shield in the region 1416 between the first and second openings. It is believed that this effect is attained by the presence of induced eddy currents in the shield region 1416 that have a vertical directional component (e.g., pointing away from and/or transverse and/or perpendicular to the plane of the shield) upon activation of the magnetic stimulators. Without wishing to be bound by theory, it is believed that the shield 1306 is configured to direct the eddy currents induced by the magnetic stimulators in the region 1416 to have a vertical component because the longitudinal channels 1412, 1414 disrupt the horizontal flow of the induced eddy currents. In the absence of the channels 1412, 1414, activation of the magnetic stimulators may induce eddy currents in the shield that only have (or predominantly have) a horizontal directional component (e.g., along and/or parallel to the plane of the shield) that encircle and/or loop around the openings. Such horizontally directed eddy currents do not form current loops transverse to the plane of the shield, but only loop along the plane of the shield. These horizontally-directed eddy currents may provide little, if any, attenuation of the magnetic field from the stimulators. In the presence of channels in the shield that intersect the openings, the induced horizontal/planar eddy currents may be disrupted by breaking the horizontally-directed current loop around the openings. This disruption may cause the eddy currents in the space between the openings to loop across the thickness of the shield (e.g., perpendicular to the plane of the shield, transverse to the plane of the shield) such that there is a vertical directional component to the eddy current flow in that region. This effect is conceptually depicted in FIGS. 15A and 15B. FIG. 15A depicts the simulated eddy currents in the shield induced during activation of two magnetic stimulators positioned over the openings (as shown in FIGS. 13A and 13B), and FIG. 15B depicts a cross-sectional view of the marked-off region in FIG. 15A. As schematically depicted in FIG. 15B, the induced eddy currents not only move horizontally along the plane of the shield, but also loop transversely to the plane of the shield (e.g., across the thickness of the shield). The vertically-directed eddy currents in the shield may counteract the magnetic field applied by the magnetic stimulators in the space between the openings such that the induced eddy current density in the tissue underneath the shield is less than it would be without the shield. While longitudinal channels that transect the entire thickness of the shield are depicted and described herein, other features may be used to disrupt the induced eddy currents in the shield to create vertically-directed eddy currents. Such features may include, but are not limited to, non-conductive barriers or dividers within the internal cavity of the shield, and internal walls integrally formed within the shield. The location of the channels and/or eddy current barriers may vary to attain the desired shielding effect, and need not intersect the openings along a central axis of the openings. In some variations, the channels and/or eddy current barriers may not completely intersect the openings (e.g., may not contact the openings), or they may intersect more than one opening (e.g., the channels and/or barriers may extend between the left and right side of the shield, thereby intersecting both openings). Additional variations are described below.

The location and size of the first and second openings 1408, 1410 may be determined at least in part by the location and size of the target neural tissue and/or the magnetic stimulators. For example, the openings may be located in the center of the shield, or may be located towards the front, back, left and/or right side of the shield, as may be desirable depending on the location of the neural region to be stimulated. The openings 1408, 1410 are depicted as having a circular shape, but may have any shape, including but not limited to, rectangular, elliptical, hexagonal, octagonal, etc., or any polygonal shape. The openings may be sized such that their longest dimension is smaller than the width of the magnetic stimulators. For example, the diameters of circular openings may be from about 10% to about 90% of the width of the magnetic stimulators, e.g., about 40% or 50% of the stimulator width. In some variations, the width of the magnetic stimulators 1302, 1304 may be about 77 mm and the diameter of the openings 1408, 1410 may be about 35 mm. Alternatively, the openings may be sized such that their longest dimension is larger than the width of the magnetic stimulators. For example, the diameters of circular openings may be from about 100% to about 200% of the width of the magnetic stimulators. The length of the space between the openings may be determined at least in part by the size of the skin surface that is desired to be shielded. Alternatively or additionally, the length of the space between the openings may be determined by the size of the region of surface tissue where the induced eddy current density would be the greatest. For example, when the stimulators 1302, 1304 are activated, they may induce eddy currents in the skin surface that lies between the two stimulators having a relatively high (and/or highest) current density of all the stimulated tissue regions. This may create a "hot spot" on the skin surface that could be painful for the patient, thereby limiting the duration and the frequency of treatment. The length of that skin surface region that is subjected to a "hot spot" of eddy current heating may be any size, for example, from about 5 mm to about 15 cm, e.g., about 30 mm, about 40 mm, about 50-60 mm. Accordingly, the size of the space between the two openings 1408, 1410 may have a length from about 3 mm to about 17 cm, e.g., about 30 mm, about 40, mm, about 57 mm. In some variations, the size of the space between the openings may depend in part on the size of the openings. For example, the space between the openings may be from about 0.5 to about 3 times the opening diameter, e.g., about 50%-300% of the opening diameter, about 125%, about 150%, about 160%, about 200%, etc. While the shield 1302 is depicted as having two openings, it should be understood that a shield for use with any of the magnetic stimulation systems described herein may have any number of openings, e.g., 1, 2, 3, 4, 5, 6, 8, 10, 12, 24, etc. arranged in any pattern across the shield according to the location of the targeted neural regions. In some variations, the number and location of shield openings may vary depending on the type of magnetic stimulator that is to be used with the shield. The shield openings may be arranged with respect to the location of an anticipated "hot spot" of relatively higher eddy current density. For example, a figure-eight stimulator may generate a "hot spot" with relatively higher eddy current density in tissue that is directly under the intersection of the two planar loops, and a magnetic stimulator may have two openings that are aligned with the two loops so that the eddy current density in the possible "hot spot" can be reduced. An H-coil where the H-shaped region is located at the top of a head model may generate a ring having a relatively high eddy current density around the head, and a magnetic stimulator may have a plurality of openings that may also be arranged in a ring that corresponds in location with the ring of relatively high eddy current density.

The shield 1302 may have a thickness (e.g., the dimension between the external surface 1402 and the internal surface 1406) that is consistent across the shield or may vary across the shield, depending on the desired level of magnetic shielding. In some variations, the shield may have a thickness between about 2 mm and about 15 mm, e.g., about 4.5 mm. Some regions of the shield may be thicker than other regions, which may provide for greater shielding of the tissue beneath the thicker region.

As briefly described above, the channels 1412, 1414 may transect the thickness of the shield 1306 and may also intersect the openings 1408, 1410. Additionally, some variations of magnetic shields may have one or more grooves, slits, gaps and the like, at various locations in the shield such that the induced eddy currents in the shield have vertically directed components that act to oppose and/or attenuate the magnetic field from the magnetic stimulators. Alternatively or additionally, the shield may comprise one or more walls or barriers or dividers in the fluid-filled cavity that extend between the external surface and the internal surface that may have a similar attenuating effect. For example, the walls or barriers in the fluid-filled cavity may be made of a non-conductive material which may act to block or obstruct eddy currents induced in the shield. The width of the channels and/or barriers may be any width that will substantially block the fluid flow and/or disrupt horizontal eddy current loops (e.g., the smallest possible width to attain these effects may be used). In some variations, the width of the channels may be from about 0.25 mm to about 5 mm, e.g., about 2 mm. The internal walls or barriers may intersect the one or more openings in the shield. In some variations, the internal walls or barriers may be integrally formed with the external surface and/or internal surface of the shield. The internal barriers and/or channels of a shield may separate the shield into separate chambers, compartments, or sections such that little or no fluid from one chamber or section is in direct communication with the fluid in another section. Such fluid separation may help to ensure that the induced eddy currents form loops that are transverse to the plane of the shield (e.g., vertically-directed) instead of currents that form loops that are parallel to the plane of the shield (e.g., horizontally-directed). For example, as seen from the top view depicted in FIG. 14B, the channels 1412, 1414 may divide the shield 1306 into three separate sections or chambers 1418, 1420, 1422. The fluid in each of these sections is not in communication with the fluid in any other section, such that currents in one section cannot form a loop with currents in another section. While total isolation and/or separation of these shield sections are depicted, in some variations, these sections may not be entirely isolated from each other. For example, a shield may have one or more channels and/or barriers that substantially impede the flow of fluid such that induced eddy currents have a substantial vertical directional component, but those channels and/or barriers may not entirely block the flow of fluid between different sections. Such channels or barriers may not entirely transect the thickness of the shield, and/or may not entirely intersect an opening (e.g., the channel or barrier may extend near an opening, but may not intersect or contact the opening). In some variations, a shield may comprise one or more sections that may be fluidly isolated from the other sections, as well as one or more sections that are not fluidly isolated from the other sections.

Channels and/or barriers that disrupt horizontally-directed eddy current loops to form vertically-directed current loops may be located at various regions on the shield. The channels 1412, 1414 of shield 1306 are located such that they extend between the front region 1403 and the back region 1405 of the shield, however, they may also extend between the right 1407 and the left 1409 regions of the shield. Each channel may intersect at least one opening, and/or may intersect two openings. For example, a channel or barrier that extends between the right and left regions of the shield 1306 may intersect both the first opening 1408 and the second opening 1410. In some variations, a first channel or barrier may extend from the back of the shield to an opening and a second channel or barrier may extend from the opening to the front of the shield, where the first and second channels are not aligned (e.g., not co-linear). In some variations, the first and second channels may be perpendicular to each other. A plurality of channels and/or barriers may be arranged to form a grid or matrix across the surface of the shield, which may divide the shield into multiple separate sections or chambers. Channels and/or barriers may also extend across the surface in a random pattern, which may act to further disrupt horizontal looping of induced eddy currents. Optionally, a shield may comprise channels or barriers that do not intersect any openings. For example, a shield may comprise one or more channels and/or barriers that entirely transect the thickness of the shield and intersect an opening as well as one or more channels that do not entirely transect the thickness of the shield and/or intersect an opening. Alternatively, a shield may comprise only channels and/or barriers that do not entirely transect the thickness of the shield and/or intersect an opening. A shield may comprise channels and/or barriers that extend across the entire length of the shield and/or may comprise channels and/or barriers that extend across only a sub-portion of the shield (e.g., the length of the channel and/or barriers may be less than the length of the shield.

A shield that comprises one or more channels that entirely transect the thickness of the shield that divide the shield into two or more separate sections may also comprise an attachment mechanism to retain the separate sections together. A shield may comprise a frame that circumscribes the lower edge of the shield. The frame may have a slot into which the lower edge of the shield may be inserted and retained (e.g., by friction-fit, snap-fit, screw-fit, adhesives, etc.). Alternatively or additionally, adhesives may be used to attach the separate sections of the shield together. For example, there may be an adhesive sheet or film that adheres to the internal surface of the shield such that all the separate sections are adhered to the sheet or film. Alternatively or additionally, the separate sections of a shield may be attached to each other via snap-fit, screw-fit, and/or friction-fit. In some variations, the separate sections may be welded together, and/or may be integrally molded. For example, the separate sections may be individual compartments that are connected by intervening segments of shell material to form the overall shield.

A magnetic shield may be positioned such that the openings of the shield are aligned with the magnetic stimulators. For example, in the stimulation system 1300, the first and second openings 1412, 1414 of the shield 1306 are aligned with the first and second magnetic stimulators 1302, 1304 such that the center of each opening is aligned with the center of the corresponding magnetic stimulator. Magnetic stimulation systems that comprise a first and second helically coiled stimulator may have a shield with first and second openings that are aligned with the center of each helical coil. While the stimulators 1302, 1304 may be helically coiled stimulators (such as those described and depicted in FIGS. 1-3), in some variations, they may be looped co-planar stimulators (such as the figure-eight coils described and depicted in FIG. 6). Magnetic stimulation systems that comprise a first and second figure-eight stimulator (which has a first loop attached to a second loop) may have a shield with first and second openings, where the first and second openings may be aligned with the center of each loop during a procedure. In some variations, the openings may not be aligned with the stimulators. For example, the figure-eight stimulator may be positioned over the shield such that the juncture between the first and second loop is located over the opening. The location of the one or more openings in a shield may vary with respect to the stimulators depending on the location and depth of the target neural tissue. For example, shields for stimulating brain tissue may have openings and channels (and/or barriers) in different locations across the plane of the shield depending on the location of the region of the brain to be stimulated. Alternatively or additionally, the magnetic stimulators may be moved relative to the openings to adjust the penetration depth of the magnetic field and/or vary the location of the tissue regions that are stimulated. Moving the magnetic stimulators relative to the openings may refine or tune the eddy current distribution in the neural tissue such that the same tissue areas experience the effect of induced eddy currents, but with different degrees of magnitude or direction. Alternatively or additionally, in the course of a treatment, different shields having openings in different locations may be used so that a practitioner can direct magnetic stimulation to multiple regions of the brain. For example, shields with different amount of spacing between the openings may be used depending on the regions of the brain that need to be shielded. In some variations, areas of the brain and/or scalp tissue that are particularly sensitive to magnetic fields (e.g., where stimulation of that region may cause pain and/or seizures) may be shielded from stimulation by using a shield where the space between the openings is positioned over the region to be protected. During use, a patient may wear the shield such that it closely contacts the skin surface (e.g., scalp). This may help facilitate the shielding effect and heat dissipation from the skin surface, as well as allow the magnetic stimulators to be positioned close to the skin surface.

FIGS. 13A-13C depict a magnetic stimulation system comprising pair of helically coiled stimulators and a shield, however, other magnetic stimulation systems may comprise stimulators with alternate geometries. For example, a magnetic stimulation system may comprise at least one H-coil and at least one shield, where the locations and number of the shield openings may correspond to the location of a ring of relatively high eddy currents in the tissue induced by the H-coil. While the magnetic stimulation system 1300 as depicted comprises two magnetic stimulators, it should be understood that a magnetic stimulation system may have more than two magnetic stimulators (e.g., 3, 4, 5, 6, 8, 10, 12 or more) or may have a single magnetic stimulator. A magnetic stimulation system having a plurality of stimulators may have a two dimensional array of stimulators. Alternatively, the plurality of stimulators may be arranged in a line (e.g., a one dimensional array). For example, a plurality of stimulators may be arranged such that they circumscribe the surface of a generally spherical magnetic shield. In some variations, the number of openings in a shield may correspond with the number of magnetic stimulators that are to be used during treatment, while in other variations, there may be a different number of openings and stimulators. Magnetic shields may be separate from the magnetic stimulators, or may be contained in the same housing as the magnetic stimulators.

As described above, the internal cavity of the shield may comprise a conductive fluid, such as saline, salt water, and the like. Optionally, the conductive fluid may comprise a material that changes its optical characteristics (e.g., color, light absorbency, refraction, etc.) as a function of the direction and/or magnitude of a magnetic field. In some variations, the conductive fluid may comprise sulfuric acid solutions containing super-paramagnetic nanoparticles. For example, the conductive fluid may comprise a super paramagnetic material, for example, iron oxide nanocrystal particles, which may change color based on the ambient magnetic field. In some variations, the iron oxide nanocrystal particles may be in clusters. For example, super paramagnetic $Fe_2O_3$ nanoparticles may form a stable particulate suspension which retains its molecular mobility character, as carried by the commonly-used inert and porous polymer, e.g. polymer of polyacrylic acid (PAA). The suspension may be elaborately adjusted to its desired homogeneity and viscosity by pH degree optimization by balancing the ratio of sulfuric acid versus NaOH/PEG (polyethelene glycol) solution. When such a suspension is exposed to a magnetic field (e.g., the magnetic field applied by one or more magnetic stimulators), the distance between the intermolecular $Fe_2O_3$ nanoparticles may change, thereby changing the color of suspension. Such a color change may act as a visible magnetic field strength marker, so the practitioner has real-time feedback about the magnetic field strength in a particular location of the shield. Magnetic compounds which may be used in a conductive fluid may include the transition metal oxides, sulfides, silicides and carbides, optionally having different transition metals in a single magnetic compound, such as $Gd_3fe_5O_{12}$. Preferred are the class of magnetic oxides known as ferrites, generally represented as $MO.Fe_2O_3$ in which M is Zn, Gd, V, Fe, Ni, Cu, Co, Mg, such as Iron(II,III) oxide ($Fe_3O_4$) and in particular magnetite ($FeO.Fe_2O_3$). The external and/or internal surfaces of the shield may be made of a transparent or translucent material, such as high density polyethylene, polyvinyl chloride, poly acrylic acid, and the like such that optical changes to the fluid may be observed. During a procedure, the practitioner may monitor the strength and/or distribution of the magnetic field that is applied to the patient by observing the color and/or changes in color of the fluid within the shield. For example, in the presence of a high-strength magnetic field, a conductive fluid such as a sulfuric acid containing iron oxide nanocrystals may change to a blue color. Areas of blue on the shield would indicate regions where the magnetic field is relatively stronger. This may help to ensure that an excessive and/or dangerous level of magnetic stimulation is not delivered to the patient, and may also help the practitioner to adjust the position of the stimulator with respect to the shield to facilitate treatment to the target tissue while reducing the exposure of non-target tissue to magnetic fields.

Figure 16A:
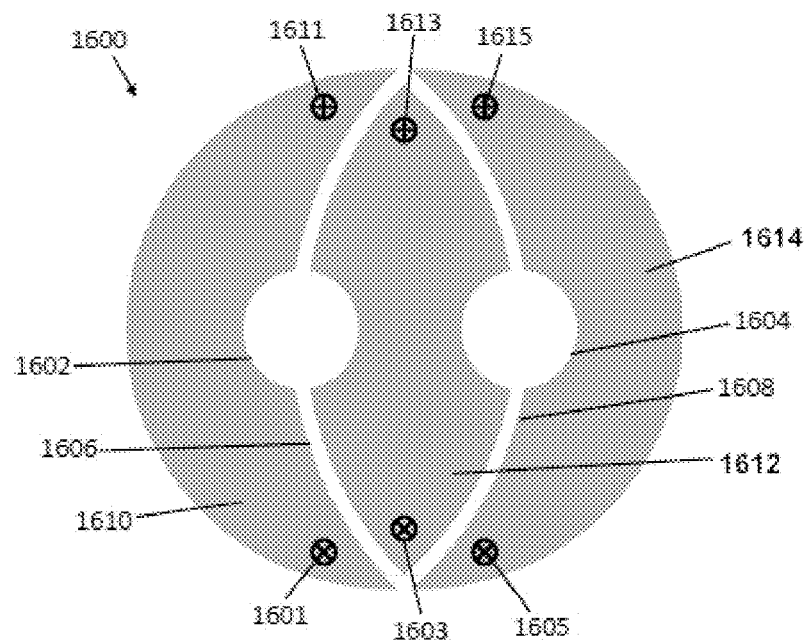
FIGS. 16A and 16B depict the top view of various shields comprising inlet and outlet ports for the circulation of the shield fluid.
Figure 16B:
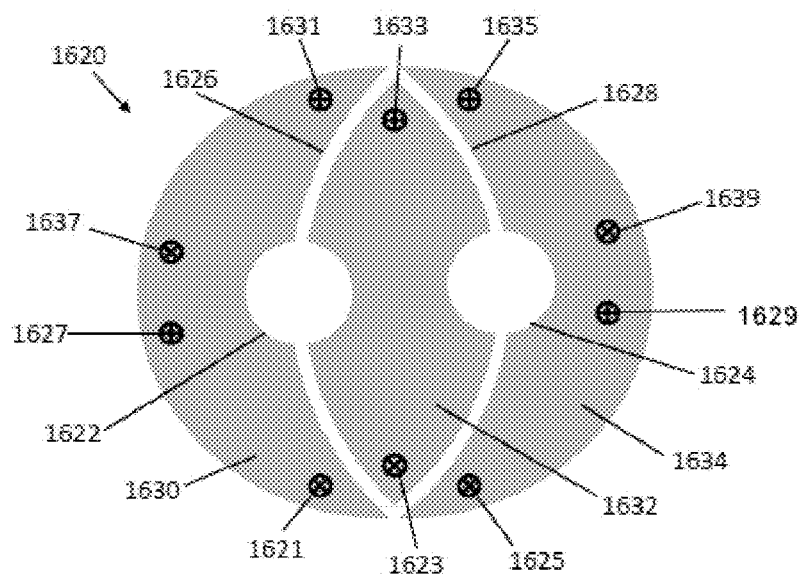

The conductive fluid within a shield may also act as a thermal sink to disperse heat generated from the magnetic stimulation (e.g., due to the induced eddy currents within the tissue). In conjunction with the vertically-directed eddy currents that counteract the magnetic field in the region(s) between openings in the shield, the conductive fluid may help to reduce the sensation of pain during a procedure by dissipating the heat resulting from induced eddy currents in the scalp. This heat dissipation may reduce the sensation of pain across the entire skin surface in contact with the shield, and facilitate with the reduction of pain due to "hot spots". This may allow the practitioner to deliver greater amounts of stimulation to the patient without increasing the sensation of pain at the skin surface. The fluid may be provided during manufacture and remain statically enclosed in the shield during use (i.e., it flows only within the shield and is not circulated outside of the shield). Optionally, in some variations, a fluid is introduced into the shield before and/or during a treatment procedure. In some variations, a shield may comprise a fluid inlet port for the ingress of fluids and a fluid outlet port for the egress of fluids. Dynamic flow of fluid into and out of the shield may facilitate the circulation of fluids within the shield such that fluid heated during magnetic stimulation is circulated out to an external heat exchanger. After the heated fluid is cooled, it is circulated back into the shield. The fluid may be circulated continuously throughout the entire duration of the treatment session, or may be circulated sporadically (e.g., periodically) during the treatment session. Each section of a shield may have a pair of inlet and outlet ports. FIGS. 16A and 16B schematically depict the top view of different variations of shields that comprise inlet and outlet ports for the circulation of the conductive fluid within the shield. FIG. 16A depicts a shield 1600 comprising a first opening 1602, a second opening 1604, a first channel or current barrier 1606, a second channel or barrier 1608, and an internal fluid-filled cavity within the wall of the shield (e.g., between the external and internal surfaces) comprising a conductive fluid (e.g., any of the conductive fluids described previously). The first channel 1606 and second channel 1608 divide the shield 1600 into a first section 1610, second section 1612, and a third section 1614. These sections may or may not be fluidly isolated from each other, and in some variations, one section may be fluidly isolated from the other section, while the other sections are fluidly connected to each other. The shield 1600 may also comprise a first fluid inlet port 1601 and a first fluid outlet port 1611 in the first section 1610, a second fluid inlet port 1603 and a second fluid outlet port 1613 in the second section 1612, and a third fluid inlet port 1605 and a third fluid outlet port 1615 in the third section 1614. While the inlet and outlet ports are depicted as being located near the edge of the shield 1600, it should be understood that any of these ports may be located at any desired region of the shield. There may also be more than one inlet and/or outlet port in each section, which may vary the rate of fluid inflow and outflow, as may be desirable. For example, FIG. 16B depicts another variation of a shield 1620 comprising a first opening 1622, a second opening 1624, a first channel or current barrier 1626, a second channel or barrier 1628, and an internal fluid-filled cavity within the wall of the shield comprising a conductive fluid. The first channel 1626 and second channel 1628 divide the shield 1620 into a first section 1630, second section 1632, and a third section 1634, where these sections may or may not be fluidly isolated as described above. The shield 1620 may also comprise a first fluid inlet port 1621 and a first fluid outlet port 1631 in the first section 1630, a second fluid inlet port 1623 and a second fluid outlet port 1633 in the second section 1632, and a third fluid inlet port 1625 and a third fluid outlet port 1635 in the third section 1634. In addition, the shield 1620 may comprise a fourth inlet port 1627 and a fourth outlet port 1637 in the first section 1630, and a fifth inlet port 1629 and a fifth outlet port 1639 in the third section 1634. These additional inlet and outlet ports may facilitate the rate of fluid circulations in those sections. An increased number of fluid ports located at various regions in the shield section may be desirable in situations where those sections cover tissue regions that are particularly sensitive to heat, and/or where a section covers a larger area, requiring more fluid circulation to attain similar levels of heat dissipation as sections with smaller areas.

Figure 17A:
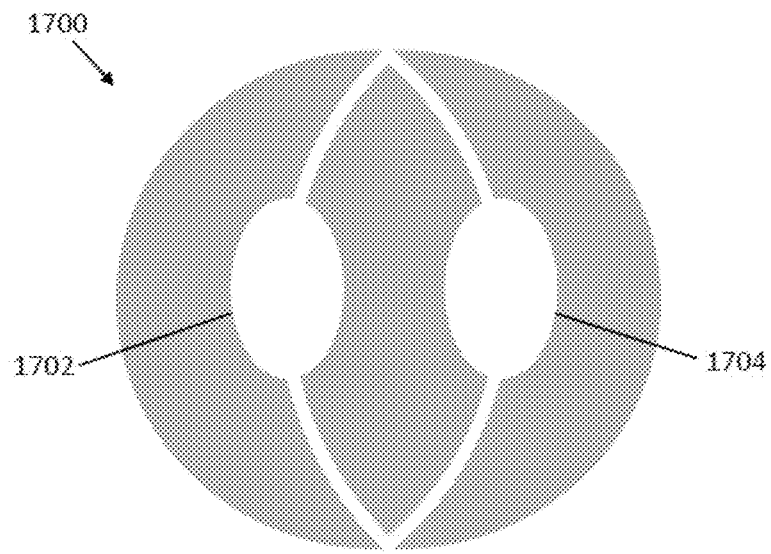
FIGS. 17A-17D depict the top view of various shields having different holes and channels.
Figure 17B:
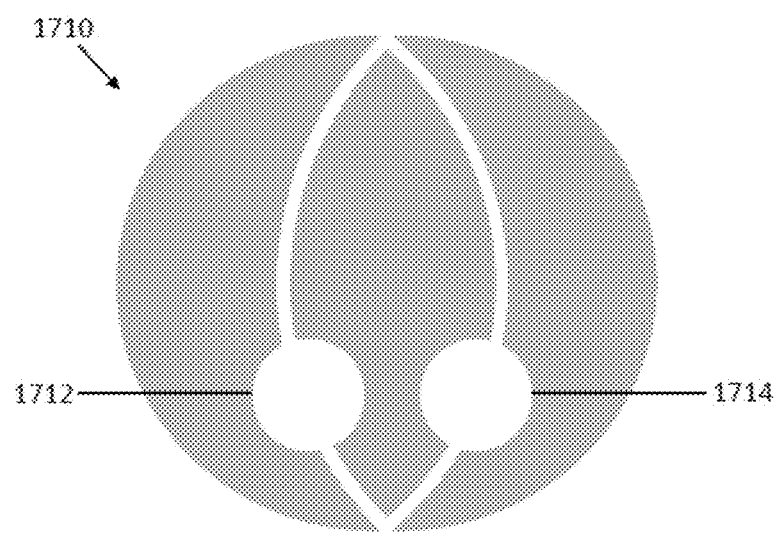
Figure 17C:
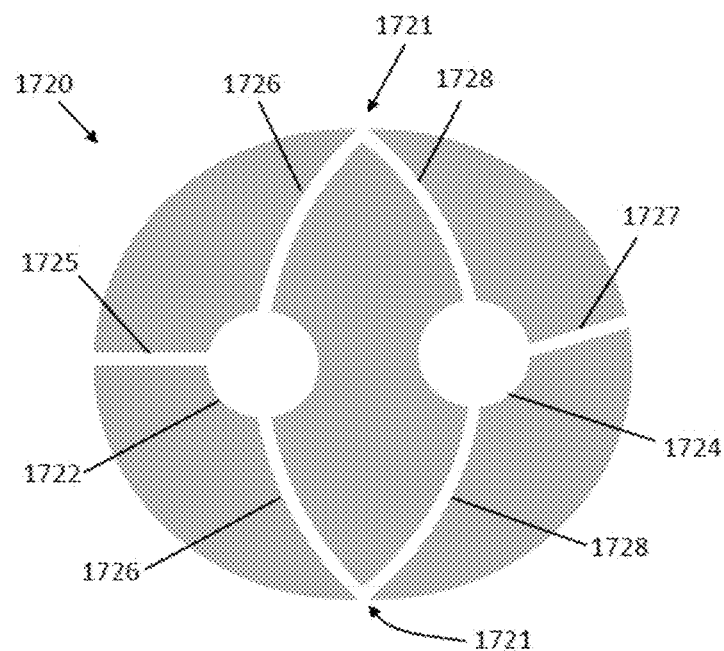
Figure 17D:
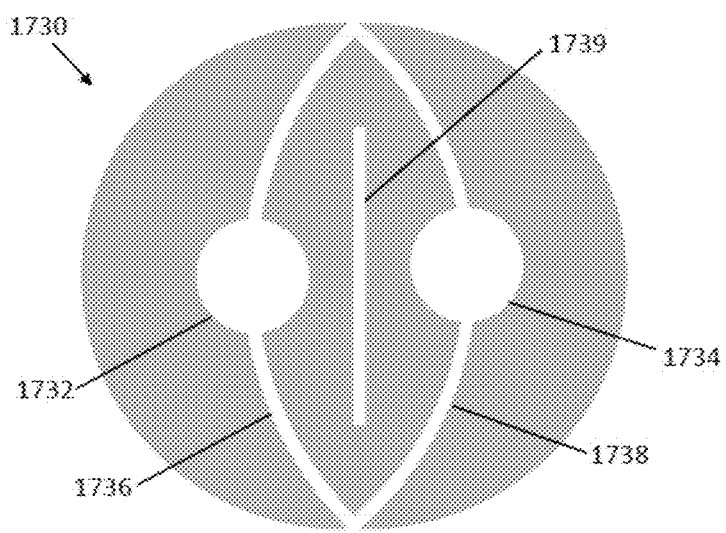

While the magnetic shields described above are depicted has having two circular openings and two channels and/or current barriers, it should be understood that a magnetic shield may have any number of openings and channels and/or current barriers, with any geometry, and located at any region in the shield. FIGS. 17A-17D depict a top view of different magnetic shield variations. FIG. 17A depicts a shield 1700 comprising two oval shaped openings 1702, 1704 located centrally on the shield. FIG. 17B depicts a shield 1710 comprising two circular openings 1712, 1714 that are located near an edge of the shield 1710. The openings in a shield may be located towards the front, back, left and/or right edges of the shield, as may be desirable to facilitate stimulation of neural tissue in those regions. FIG. 17C depicts a shield 1720 that comprises two openings 1722, 1724, a first channel and/or current barrier 1726, a second channel and/or current barrier 1728, a third channel and/or current barrier 1725, and a fourth channel and/or current barrier 1727. The channels may all intersect at least one opening. The first channel 1726 and the second channel 1728 may extend along the entire length of the shield (e.g., from the front to the back of the shield), and may converge at the edge 1721 of the shield. The third channel 1725 may intersect the first opening 1722 in a direction that is perpendicular to the first channel 1726. The fourth channel 1727 may intersect the second opening 1724 in a direction that is at an angle relative to the second channel 1728 (e.g., offset from an axis of symmetry of the opening 1724). Channels may extend along a length that is shorter than the length of the shield, and may extend between the left and right edges of the shield. FIG. 17D depicts a top view of a shield 1730 that comprises two openings 1732, 1734, a first channel and/or current barrier 1736, a second channel and/or current barrier 1738, and a third channel and/or current barrier 1739. While the first and second channels intersect the first and second openings respectively, the third channel 1739 does not intersect any openings. The length of the third channel 1739 may be less than the length of the overall shield 1730. While the third channel 1739 is depicted along an axis of symmetry of the shield 1730, it may be located at any region of the shield and may have any orientation. The location and/or orientation of the channels and/or openings may or may not be symmetric (e.g., radially or bilaterally symmetric) with respect to the overall shield shape. While the overall shape of the shields depicted herein are configured for use over a patient's head, shields may be shaped to accommodate any anatomical region as may be desirable. For example, a shield may be elongated such that it can be applied around a patient's torso for shielding and shaping magnetic stimulation of peripheral nerves and/or organs. The overall shape of the shield may vary, and in some variations, may be as small as the size of a single magnetic stimulator and may be as large as the entire anatomical structure that is to be treated. In some variations, the shield may be enclosed in a helmet that is worn by the patient, where the magnetic stimulators may be enclosed in the helmet, or separately disposed from the helmet. It should be understood that any of the features described and depicted in any one shield embodiment may be included (alone or in combination) with any of the features described and depicted in a different shield embodiment.

Figures 18A, 18C:
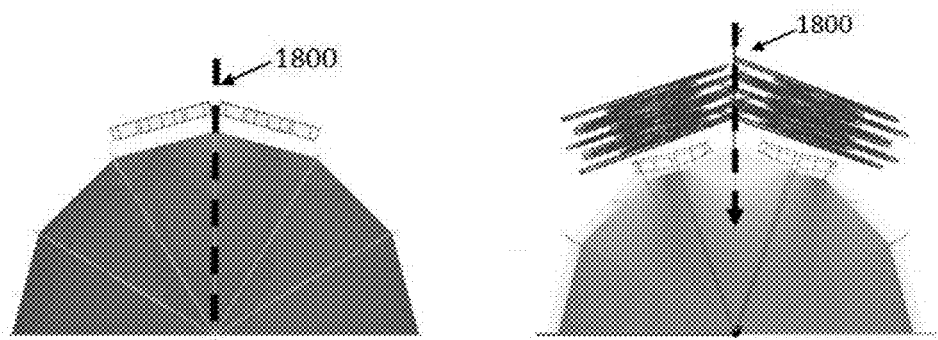
FIGS. 18A-18C depict the side view of three different magnetic stimulation systems and the eddy current distribution and density in a simulated head model.
Figure 18B:
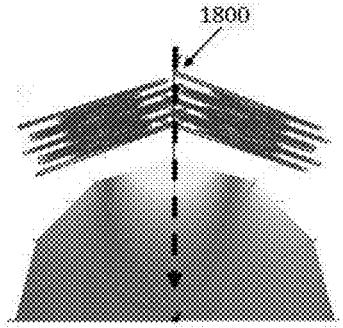
Figure 18D:
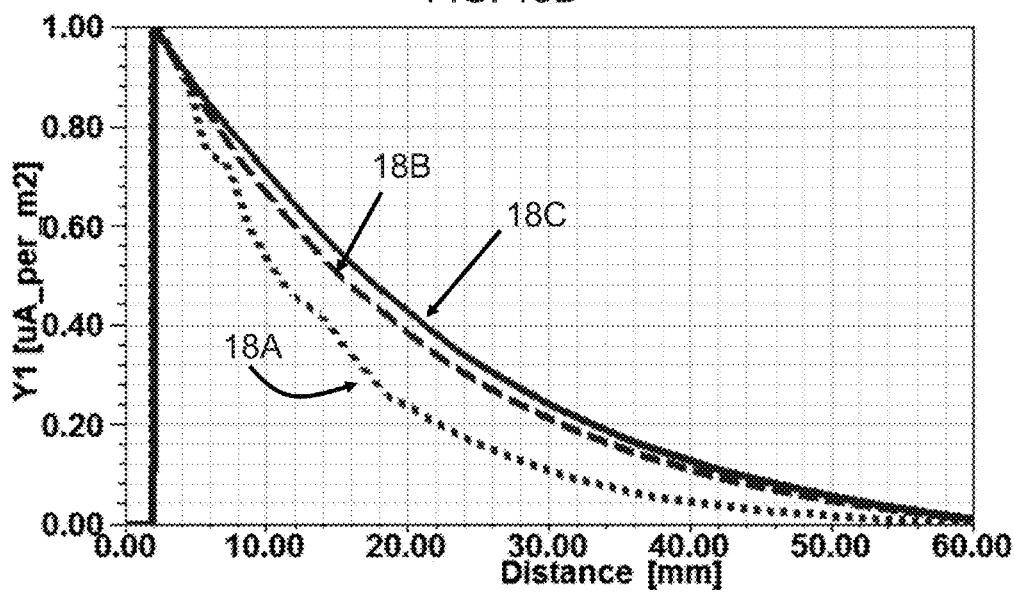
FIGS. 18D and 18E depict normalized plots that represent eddy current density as a function of skull depth.
Figure 18E:
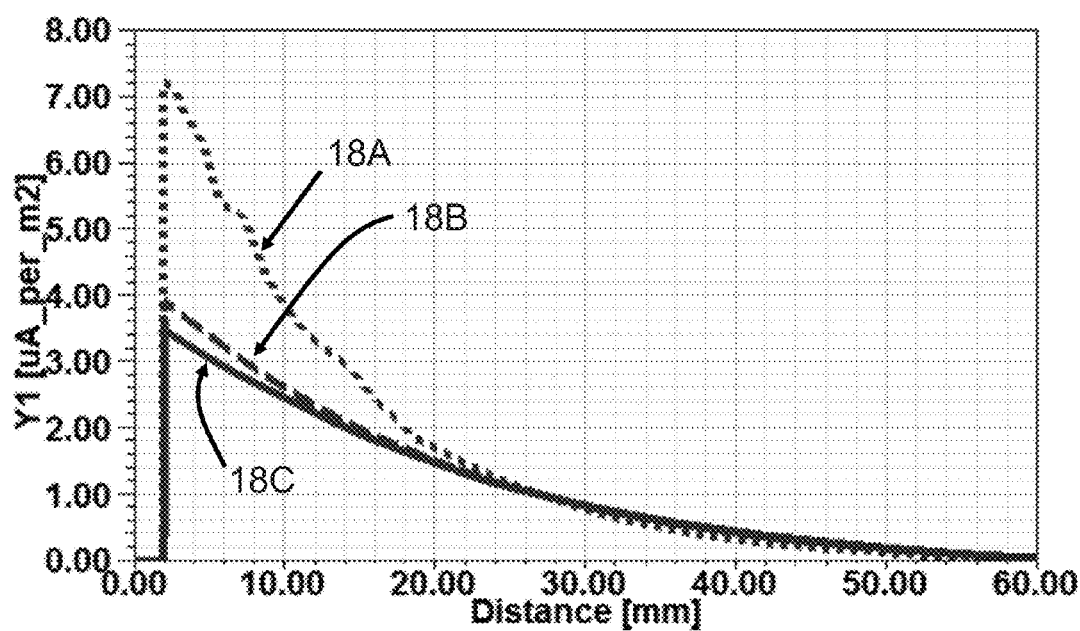

The distribution of induced eddy currents in brain tissue using different magnetic stimulation systems was simulated on a microprocessor. FIGS. 18A-18E depict the simulation results for magnetic stimulations systems that comprise different stimulators and shields. FIG. 18A depicts the eddy current distribution in a head model induced by a magnetic stimulation system comprising a figure-eight stimulator. FIG. 18B depicts the eddy current distribution in a head model induced by a magnetic stimulation system comprising two helically coiled stimulators. FIG. 18C depicts the eddy current distribution in a head model induced by a magnetic stimulation system comprising two helically coiled stimulators and the shield described above and depicted in FIGS. 14A-14D. Simulation parameters for the cortical bone of the skull and brain white matter, as well as the current applied to the simulators were the same as previously described (see FIGS. 4A-4D). FIG. 18D depicts a plot of the normalized eddy current density (i.e., eddy current density is normalized to the maximum eddy current density value at the surface of the head model) in the white matter of the head model as a function of the depth into the head (along the line denoted by arrow 1800, which is along a line of symmetry for both the figure-eight and helically coiled stimulators). The line with short dashes represents the eddy current density induced by the magnetic stimulation system of FIG. 18A, the line with long dashes represents the eddy current density induced by the magnetic stimulation system of FIG. 18B, and the solid line represents the eddy current density induced by the magnetic stimulation system of FIG. 18C. Although the eddy current density is the same for all three systems at the surface of the head (e.g., the scalp), the current density decreases at a greater rate for the figure-eight stimulation system (18A) than for the either of the helically coiled systems (18B and 18D). The current density for the FIG. 18C system does not decrease as much as the current density for the FIG. 18B system. For example, at a head depth of about 25 mm, the eddy current density for the figure-eight stimulation system is about 16% of the surface eddy current density, while the eddy current density for the helical coil stimulation system without shielding is about 24% of the surface eddy current density, and the eddy current density for the helical coil stimulation system with shielding is about 33% of the surface eddy current density. For the system of FIG. 18A, the eddy current density is reduced to 20% of the scalp current density at a depth of about 22 mm, however, for the system of FIG. 18C, the eddy current density is reduced to 20% of the scalp current density at a depth of about 33 mm. Put another way, with the same amount of current applied to the stimulators of the three different systems, the magnitude of the eddy current density induced by the FIG. 18C system is greater at a deeper depth into the white matter of the head model as compared to the eddy current density induced by the FIG. 18A and FIG. 18B systems (which do not have shielding). FIG. 18E depicts a plot of the normalized eddy current density (i.e., eddy current density is normalized to the same eddy current density value at a depth of 25 mm) in the white matter of the head model as a function of the depth into the head. In order for the FIG. 18A system to attain the same eddy current density at a depth of 25 mm as the FIG. 18C system, the eddy current density at the surface of the head needs to be about two times the eddy current density of the FIG. 18C system. That is, a greater amount of current would need to be applied to the figure-eight stimulators than the amount of current that needs to be applied to the helical coils of the FIG. 18C stimulation system. In other words, using the FIG. 18C system instead of the FIG. 18A system would decrease the surface eddy current by about 50%. Reducing the surface eddy current by about 50% may also reduce the amount of heat experienced by the patient at the scalp, which would help reduce the sensation of pain or discomfort.

Described herein are kits for the treatment of neurological disorders using magnetic stimulation. One variation of a kit may comprise one or more types of magnetic stimulators. For example, a kit may comprise at least one helically coiled stimulator, and may optionally comprise at least one of a figure-eight stimulator. Another variation of a kit may comprise at least one stimulator and at least one shield. For example, a kit may comprise at least one helically coiled stimulator and the shield depicted in FIGS. 14A-14D. Optionally, a kit may comprise at least one helically coiled stimulator and a plurality of shields, where the openings and/or channels in the shield may vary for each shield. For example, the location of the openings in each shield of the kit may be different in order to allow the practitioner to select the shield with the openings located in the proximity of the target tissue. The size and shape of the shields, location and number of channels in each shield, number of fluid inlets and outlets in each shield, and other features that have been previously described may be different for each shield in the kit. The one or more magnetic shields in a kit may be already pre-filled with a conductive fluid, or may not be filled with a conductive fluid (in such case, the conductive fluid is introduced into the shield just prior or during treatment).

The magnetic neural stimulation systems described herein may be used to stimulate peripheral nerves and/or nerves of the autonomic system, including the brain and spine. For example, a neural stimulation system for the targeted stimulation of renal nerves may comprise one or more helical coils having a plurality of acute turns, and may optionally comprise one or more cylindrical shielding components. The size, number of turns, and placement of the helically coiled stimulator with respect to the renal nerves may be adjusted to efficiently stimulate the renal nerves while reducing stimulation to adjacent tissue. Other nerves that may be stimulated using any of the stimulators and/or shielding components disclosed herein include the celiac plexus, aorticorenal ganglion, the aortic plexus, etc. The magnetic stimulation systems described herein may also be used in the treatment of various types of neurological disorders/disease in all areas of the body, including, but not limited to: vagus nerve disorders/diseases (which may spread along the area of tissues or organs innervated by the vagus nerve, extending from the brain to the abdomen), spinal cord and peripheral nerve disorders, back and joint pains related to neural disorders, heart arrhythmia and heart nerve pain, pelvic neuropathy related to fecal or bladder incontinence, headaches, migraines, depression, obsessive-compulsive disorder, insomnia, bipolar disease, post-traumatic stress syndrome, Parkinson's disease, schizophrenia, dystonia, autism, pain, and epileptic or febrile seizures, etc. The magnetic stimulation systems described herein may also be used in the treatment of other diseases, including tumors in different states of progression and various autoimmune diseases (e.g. multiple sclerosis, disabling rheumatoid arthritis, etc.).

What is claimed is:
1. A magnetic stimulation system comprising:
a first coil comprising a single wire having a plurality of turns; and a shield comprising:
- an external surface and an internal surface both comprising a non-conductive material, wherein the first coil is disposed above the external surface;
- an internal cavity defined between the external surface and the internal surface;
- a first opening, penetrating through the shield and communicating the external surface and the internal surface; and
- a first channel, formed on the external surface and intersecting the first opening, wherein a depth of the first channel extends through an entire thickness of the shield to divide the internal cavity; and
- a conductive substance, filled in the internal cavity.

2. The magnetic stimulation system of claim 1, wherein the conductive substance is a conductive fluid.

3. The magnetic stimulation system of claim 2, wherein the conductive fluid comprises a super-paramagnetic compound.

4. The magnetic stimulation system of claim 3 wherein the super-paramagnetic compound is a magnetic oxide ($MO-Fe_2O_3$), where M is selected from the group consisting of Zn, Gd, V, Fe, Ni, Cu, Co, Mg.

5. The magnetic stimulation system of claim 2, wherein the conductive fluid comprises saline.

6. The magnetic stimulation system of claim 2, wherein the shield further comprises an inlet port for ingress of the conductive fluid and an outlet port for egress of the conductive fluid.

7. The magnetic stimulation system of claim 6, wherein the inlet port and the outlet port are configured to be connected to a heat exchanger, wherein the heat exchanger is configured to cool the conductive fluid received from the outlet port and transport the cooled conductive fluid to the inlet port.

8. The magnetic stimulation system of claim 1, wherein the external and internal surfaces of the shield are made of a transparent material.

9. The magnetic stimulation system of claim 8, wherein the transparent material is high density polyethylene.

10. The magnetic stimulation system of claim 8, wherein the transparent material is polyvinyl chloride.

11. The magnetic stimulation system of claim 8, wherein the transparent material is poly acrylic acid.

12. The magnetic stimulation system of claim 1, wherein the first channel is configured to shape current flow through a conductive fluid such that the direction of the current flow has a vertical component that is perpendicular to the external and/or internal surfaces of the shield.

13. The magnetic stimulation system of claim 1, wherein each turn of the first coil has a turning angle of less than 90 degrees.

14. The magnetic stimulation system of claim 1, wherein the first coil has a first end and a second end, wherein the first end is configured to be connected to a positive terminal of a high voltage source and the second end is configured to be connected to a negative terminal of the high voltage source.

15. The magnetic stimulation system of claim 1, further comprising a second coil adjacent to and connected in series with the first coil, and
wherein the shield further comprises
- a second opening penetrating through the shield and communicating the external surface and the internal surface; and
- a second channel formed on the external surface and intersecting the second opening, and a depth of the second channel extends through the entire thickness of the shield to divide the internal cavity.

16. The magnetic stimulation system of claim 15, wherein the first and the second openings are circular and have a diameter that is less than a diameter of the first and the second coils.

17. The magnetic stimulation system of claim 15, wherein a separation between the first and second openings is less than or equal to a radius of the first and second coils.

18. The magnetic stimulation system of claim 1, further comprising at least two more coils adjacent to each other and connected in series with the first coil, and
wherein the shield further comprises
- additional openings for each of the at least two more coils respectively to penetrate through the shield and communicating the external surface and the internal surface; and
- additional channels for the additional openings formed on the external surface and intersecting the openings, and a depth of the additional channels extending through the entire thickness of the shield to divide the internal cavity.

* * * * *